US008481256B2

(12) United States Patent
Lacal Sanjuan et al.

(10) Patent No.: US 8,481,256 B2
(45) Date of Patent: Jul. 9, 2013

(54) IN VITRO METHOD FOR IDENTIFYING COMPOUNDS FOR CANCER THERAPY

(75) Inventors: Juan Carlos Lacal Sanjuan, Madrid (ES); Ana Ramirez de Molina, Madrid (ES); David Gallego Ortega, Madrid (ES); Mónica Bañez Coronel, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 674 days.

(21) Appl. No.: 11/911,513

(22) PCT Filed: Apr. 12, 2006

(86) PCT No.: PCT/ES2006/070047
§ 371 (c)(1),
(2), (4) Date: Jul. 1, 2009

(87) PCT Pub. No.: WO2006/108905
PCT Pub. Date: Oct. 19, 2006

(65) Prior Publication Data
US 2009/0304575 A1 Dec. 10, 2009

(30) Foreign Application Priority Data
Apr. 13, 2005 (ES) .................................. 200500875

(51) Int. Cl.
*C12Q 1/00* (2006.01)
*C12Q 1/68* (2006.01)
*G01N 33/53* (2006.01)

(52) U.S. Cl.
USPC ........................................... 435/6.1; 435/7.1

(58) Field of Classification Search
None
See application file for complete search history.

(56) References Cited

U.S. PATENT DOCUMENTS
2003/0186241 A1 10/2003 Dai

FOREIGN PATENT DOCUMENTS
| ES | 2277568 A1 | 7/2007 |
| JP | 11510393 A | 9/1999 |
| JP | 2004515225 A | 5/2004 |
| JP | 2004201684 A | 7/2004 |
| JP | 2005073548 A | 3/2005 |
| WO | 9400603 A1 | 1/1994 |
| WO | 9706256 A2 | 2/1997 |
| WO | 0221996 A2 | 3/2002 |
| WO | 2005001089 A | 1/2005 |

OTHER PUBLICATIONS

Nakagami et al (Japan J Cancer Research, 1999, 90:419-424; abstract only) 1 page.*
Molina et al (Biochemical and Biophysical Research Communications, 2002, 296:580-583).*
Bernard et al (Clinical Chemistry, 2002, 48:1178-1185).*
Aoyama, C. Liao, H., Ishidate, K. Structure and function of choline kinase isoforms in mammalian cells. Progress in Lipid Research, May 2004,vol. 43. No. 3, pp. 266-281, ISSN 0163-7827.
Hernandez-Alcobea, R., Fernadez, F., Lacal, J. C. In vivo antitumor activity of choline kinase inhibitors: a novel target for anticancer drug discovery. Cancer Research. Jul. 1999,vol. 59. No. 13,pp. 3112-3118. ISSN 0008-5472.
Nakagami K., Uchida, T., Ohwada, S. et. al. Increased choline kinase activity and elevated phosphochline levels in human colon cancer. Japanese Journal of Cancer Research. Apr. 1999.vol. 90, No. 4, pp. 419-424. ISSN 0910-5050.
Ramirez De Molina, A., Rodriguez-Gonzalez, A., Gutierrez, R. et. al. Overexpression of choline kinase is a frequent feature in human tumor-derived cell lines and in lung, prostate, and colorectal human cancers. Biochemical and Biophysical Research Communications. Aug. 2002.vol. 296. No. 3, pp. 580-580. ISSN 0006-291X.
Nakagami K., Uchida, T., Ohwada, S. et. al. Increased choline kinase activity in 1,2-dimethylhydrazine-induced rat colon cancer. Japanese Journal of Cancer Research. Nov. 1999, vol. 90 No. 11, pp. 1212-1217, ISSN 0910-5050.
Ramirez De Molina, A., Banez-Coronel, M., Gutierrez, R., et. al. Choline kinase activation is a critical requirement for the proliferation of primary human mammary epithelial cells and breast tumor progression. Cancer Research. Sep. 2004. vol. 64. No. 18, pp. 6732-6739. ISSN 008-5472.
Aoyama C. et al.; "Structure and function of choline kinase isoforms in mammalian cells," Progress in Lipid Research, 2004, pp. 266-281, vol. 43.
Hernandez-Alcoceba R. et al.; "In Vivo Antitumor Activity of Choline Kinase Inhibitors: A Novel Target for Anticancer Drug Discovery," Cancer Research, 1999, pp. 3112-3118, vol. 59.
Nakagami K. et al.; "Increased Choline Kinase Activity and Elevated Phosphocholine Levels in Human Colon Cancer," Japanese Journal of Cancer Research, 1999, pp. 419-424, vol. 90.
Ramirez De Molina A. et al.; "Overexpression of choline kinase is a frequent feature in human tumor-derived cell lines and in lung, prostate, and colorectal human cancers," Biochemical and Biophysical Research Communications, 2002, pp. 580-583, vol. 296.
Nakagami K. et al.; "Increased Choline Kinase Activity in 1,2-Dimethylhydrazine-induced Rat Colon Cancer," Japanese Journal of Cancer Research, 1999, pp. 1212-1217, vol. 90.
Ramirez De Molina A. et al.; "Choline Kinase Activation Is a Critical Requirement for the Proliferation of Primary Human Mammary Epithelial Cells and Breast Tumor Progression," Cancer Research, 2004, pp. 6732-6739, vol. 64.

(Continued)

*Primary Examiner* — Laura B Goddard
(74) *Attorney, Agent, or Firm* — Tristan A. Fuierer; Andrew D. Gerschutz; Moore & Van Allen, PLLC

(57) ABSTRACT

The present invention relates to an in vitro method for identifying and evaluating compounds useful in the treatment of different types of cancer, especially lung, breast, colorectal and bladder cancer in an individual, for determining the stage or severity of said cancer in the individual, or for monitoring the effect of the therapy administered to an individual having said cancer; to finding, identifying, developing and evaluating the efficacy of compounds for the therapy of said cancer, for the purpose of developing new medicinal products; as well as to agents inhibiting the expression and/or activity of the choline kinase alpha protein and/or the effects of this expression.

6 Claims, 27 Drawing Sheets

OTHER PUBLICATIONS

Ramirez De Molina A. et al.; "Increased choline kinase activity in human breast carcinomas: clinical evidence for a potential novel antitumor strategy," Oncogene, 2002, pp. 4317-4322, vol. 21.

Glunde K. et al.; "Choline kinase alpha in cancer prognosis and treatment," Lancet Oncology, 2007, pp. 855-857, vol. 8.

Ramirez De Molina A. et al.; "Expression of choline kinase alpha to predict outcome in patients with early-stage non-small-cell lunch cancer: a retrospective study," Lancet Oncology, 2007, pp. 889-897, vol. 8.

Moonen et al.; Prognostic Value of p53 for High Risk Superficial Bladder Cancer With Long-Term Followup, Journal of Urology, 2007, pp. 80-83, vol. 177.

Vicini et al,; "Limitations in the Use of Serum Prostate Specific Antigen Levels to Monitor Patients After Treatment for Prostate Cancer," Journal of Urology, 2005, pp. 1456-1462, vol. 173.

Rego et al,; "Activated EGFR as a prognostic marker in human colon cancer," Journal of Clinical Oncology, 2008, 15S, vol. 26.

Cuadrado A. et al.; Phosphorylcholine: a novel second messenger essential for mitogenic activity of growth factors, Oncogene, 1993, pp. 2959-2968, vol. 8.

Jimenez B. et al.; "Generation of Phosphorylcholine as an Essential Event in the Activation of Raf-1 and MAP-Kinases in Growth Factors-Inducted Mitogenic Stimulation," Journal of Cellular Biochemistry, 1995, pp. 141-149, vol. 57.

Hernandez-Alcoceba R. et al.; "Choline kinase inhibitors as a novel approach for antiproliferative drug design," Oncogene, 1997, pp. 2289-2301, vol. 15.

Rodriguez-Gonzalez A. et al.; "Inhibition of choline kinase as a specific cytotoxic strategy in oncogene-transformed cells," Oncogene, 2003, pp. 8803-8812, vol. 22.

Rodriguez-Gonzalez A. et al.; Choline kinase inhibition induces the increase in ceramides resluting in a highly specific and selective cytotoxic antitumoral strategy as a potential mechanism of action, Oncogene, 2004, pp. 8247-8259, vol. 23.

Rodriguez-Gonzalez A. et al.; "Inhibition of choline kinase renders a highly selective cytotoxic effect in tumour cells through a mitochondrial independent mechanism," International Journal of Oncology, 2005, pp. 999-1008, vol. 26.

Moonen, et al., Prognostic value of p53 for high risk superficial bladder cancer with long-term followup, The Journal of Urology, Jan. 2007, vol. 177, pp. 80-83.

Vicini, et al., Limitations in the use of serum prostate specific antigen levels to monitor patients after treatment for prostate cancer, The Journal of Urology, May 2005, vol. 173, pp. 1456-1462.

Rego, et al., Activated EGFR as a prognostic marker in human colon cancer, Journal of Clinical Oncology, 2008 (May 20 Supplement), vol. 26, No. 155, p. 22119.

* cited by examiner

| ChoKα | Frequency | Percentage |
|---|---|---|
| Negative | 19 | 38 |
| Positive | 31 | 62 |
| Total | 50 | 100 |

| Choko | Frequency | Percentage |
|---|---|---|
| Negative | 1 | 3 |
| Positive | 37 | 97 |
| Total | 38 | 100 |

| DNA | Tumor incidence | Tumor volume (cm³) |
|---|---|---|
| PCDNAIIIb (control) | 0/24 (0 %) | 0 |
| ChoKα | 8/30 (26 %) | 0.7 ± 0.4 |

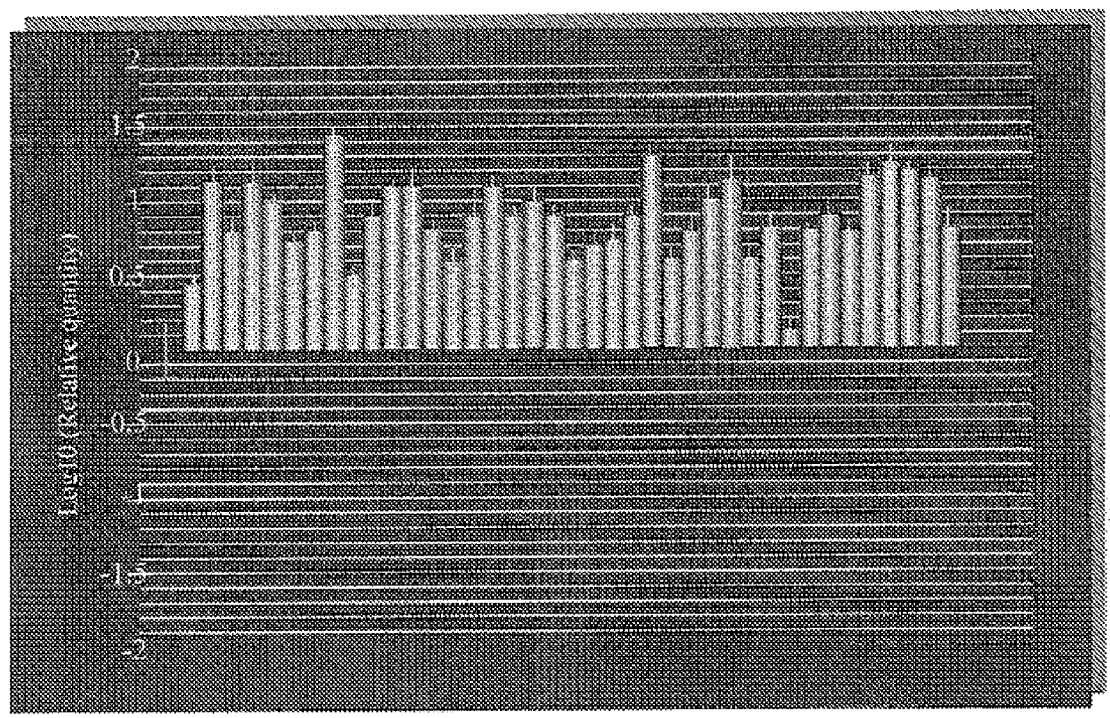
Figure 15a
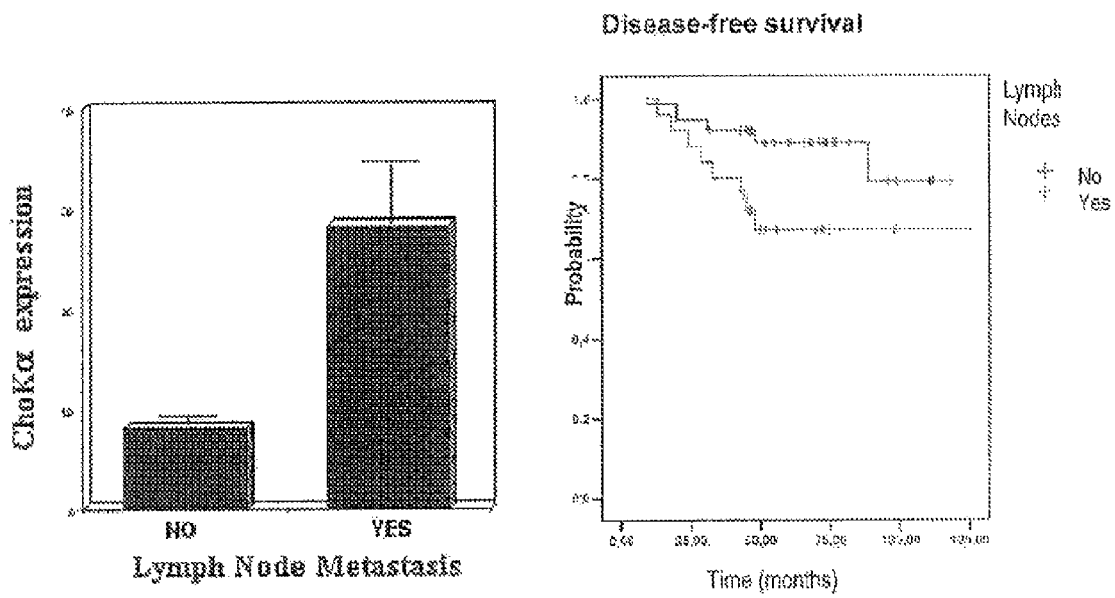
Figure 15b
Figure 15c

IN VITRO METHOD FOR IDENTIFYING COMPOUNDS FOR CANCER THERAPY

CROSS-REFERENCE TO RELATED DOCUMENTS

The present patent application claims the benefit of International Application Number PCT/ES2006/070047 with an International Filing Date of Apr. 12, 2006, which claims a Priority Date of Apr. 13, 2005. The prior application is incorporated herein in its entirety by reference.

FIELD OF THE INVENTION

The present invention relates to a method for identifying and evaluating the efficacy of compounds for cancer therapy, especially for lung, breast or colorectal cancer, for the purpose of developing new medicinal products; as well as to agents inhibiting the expression and/or the activity of the choline kinase alpha protein and/or the effects of this expression.

BACKGROUND OF THE INVENTION

Choline kinase (also known as CK, CHK and ChoK) is the initial enzyme of the Kennedy or phosphatidylcholine (PC) synthesis pathway and phosphorylates choline to phosphorylcholine (PCho) in the presence of magnesium ($Mg^{2+}$) using adenosine 5'-triphosphate (ATP) as a phosphate group donor. The transformation mediated by various oncogenes induces high levels of choline kinase activity, giving rise to an abnormal increase in the intracellular levels of its product, PCho, which indirectly supports the role of choline kinase in generating human tumors. However, there are alternative PCho generation mechanisms that do not involve the activation of choline kinase and could explain the high levels of this metabolite in tumor cells.

Although there is evidence of increase in activity of the enzyme choline kinase in tumors and transformed cells, its relationship to the carcinogenic process is not sufficiently demonstrated as no clear cause-effect relationship has been established between the increase in activity and the tumor transformation. On the other hand, the molecule responsible for this effect has still not been identified.

About 200 gene sequences encoding for polypeptides with a primary structure homologous to choline kinase have been identified and are designated as choline kinase alpha a, choline kinase alpha b, choline kinase alpha 3, choline kinase beta 1, choline kinase beta 2, choline kinase CKB-1 Choline/ethanolamine kinase, choline kinase-like ethanolamine kinase, Cots, Duff227, Cog3173 CPT1B, SF1, SHOX2, FHOD2, FLJ12242, KRTS, FBL, ARL6IP4, etc. both in humans and in other mammals and rodents (rats, mice, cows, guinea pigs, rabbits, monkeys). In fact, since 1982 there has been biochemical evidence that in different tissues isolated from rats, mice and humans there are at least three isoenzymes with choline kinase activity showing different physicochemical properties.

At least 3 genes encoding for proteins with demonstrated choline kinase activity have recently been identified in human genoma, designated as ck-alpha, ck-beta, and HCEKV (USA patent US2003186241), and several genes the encoded proteins of which are 30-65% homologous to those encoded by the ck genes, such as for example the genes CAI16602, CHKL, CAI16600, CAI16599, CAH56371, CAI16603, BAA91793, CAI16598 and the genes CPT1B, EKI2, SF1, SHOX2, FHOD2, FLJ12242, KRTS, FBL, ARI61p$, TOMM40, MLL. A very relevant characteristic of the different choline kinase isoenzymes is that they have different biochemical properties, with important variations in their affinity for the choline substrate or for the ATP phosphate donor, and even in their active form, which can be presented as dimers or tetramers. Therefore it is necessary to define if there is a direct relationship between any of the different choline kinase isoenzymes identified and the attributed tumorigenic capacity due to their overexpression in human tumors.

On the other hand, choline kinase inhibition has been demonstrated to be a new and effective anti-tumor strategy in cells transformed by oncogenes, which has been extrapolated to nude mice in vivo. The increase in choline kinase activity in several human breast carcinomas has recently been published, and it has been seen that the choline kinase alteration is a frequent event in some human tumors such as lung, colorectal and prostate tumors.

Despite the correlation between some parameters and others, there is currently no evidence definitely establishing that the overexpression of choline kinase has oncogenic and tumor activity in human cells. There is evidence indicating that choline kinase activity inhibitors, such as hemicholinium-3[Cuadrado A., Carnero A., Dolfi F., Jiménez B. and Lacal J. C. Oncogene 8, 2959-2968 (1993); Jiménez B., del Peso L., Montaner S., Esteve P. and Lacal J. C. J. Cell Biochem. 57, 141-149 (1995); Hernández-Alcoceba, R., Saniger, L., Campos, J., Núñez, M. C., Khaless, F., Gallo, M. A., Espinosa, A, Lacal, J. C. Oncogene, 15, 2289-2301 (1997)] or the low-toxicity methylenequinones in Spanish patent application ES200503263, present anti-tumor activity. However, there is no conclusive evidence in the mentioned documents or in the rest of the prior art as regards to the various isoenzymes with demonstrated choline kinase activity (ck-alpha, ck-beta, HCEKV, etc) and identified in human tissues could be responsible for the detected enzymatic activity, nor is it indicated which of the isoenzymes is sensitive to the inhibition by inhibitors which have shown anti-tumor activity. This identification is necessary in order to be able to establish its potential use as a therapeutic target in cancer.

OBJECT OF THE INVENTION

The main object of the present invention is an in vitro method to find, identify and evaluate the effectiveness of compounds for cancer therapy, especially for lung, breast or colorectal cancer.

A further object of the invention is based on the use of nucleotide or peptide sequences derived from the choline kinase alpha gene in methods for finding, identifying, developing and evaluating the effectiveness of compounds for cancer therapy, preferably for lung, breast or colorectal cancer.

Another object of the present invention consists of providing agents characterized in that they inhibit the expression and/or the activity of the choline kinase alpha protein for the treatment of cancer, preferably lung, breast or colorectal cancer.

Another object of the invention is a pharmaceutical composition comprising one or several therapeutic agents together with a pharmaceutically acceptable excipient for the treatment of cancer, preferably lung, breast or colorectal cancer.

An in vitro method for monitoring the effect of a therapy administered to a cancer patient is also object of the present invention, characterized in that the evaluation of the choline kinase alpha protein expression level in a tissue sample extracted from the patient who is being administered an antitumor agent, preferably an agent according to claims 3-5, by means of the determination in said sample of at least one parameter related to the choline kinase alpha protein which is selected from the level of its messenger RNA, the concentration of said protein or its enzymatic activity, and the comparison of the value obtained with the value corresponding to one or more normal, non-cancerous tissue samples.

Finally, another object of the present invention consists of a diagnostic kit to carry out the present invention.

DESCRIPTION OF FIGURES

FIG. 15: Choline kinase alpha overexpression in breast cancer tissue. FIG. 15a: choline kinase alpha messenger RNA in tissues of patients with breast cancer detected by real-time quantitative PCR, represented as the base 10 logarithm between the amount detected and the amount present in a normal tissue sample. FIG. 15b: mean value of choline kinase alpha expression, represented as the relative expression units of the gene calculated from the mRNA level with the $2^{-\Delta\Delta ct}$ method) in individuals without metastasis (first bar, marked as "NO") or with metastasis (second bar, marked as "YES"). FIG. 15c: evolution of the probability of survival without disease according to the number of elapsed months in the patients with lymphatic nodes (lower line, marked with gray strokes, ‡) or without lymphatic nodes (upper line, marked with black strokes, †).

FIG. 16: Choline kinase alpha expression in cell lines derived from lung cancer. FIG. 16b: choline kinase alpha protein detected by immunoassay with a monoclonal antibody in normal bronchial epithelial cells (BEC) and in cell lines derived from lung cancer H460, H1299, H510 and H82; the signal obtained for tubulin in these same samples is represented immediately under that.

FIG. 19: Choline kinase alpha expression in cell lines derived from bladder cancer.

FIG. 20: Choline kinase alpha expression in patients with bladder cancer.

FIG. 21: Relationship between choline kinase alpha expression and the presence of nodes and/or metastasis.

DETAILED DESCRIPTION OF THE INVENTION

Figure 1:
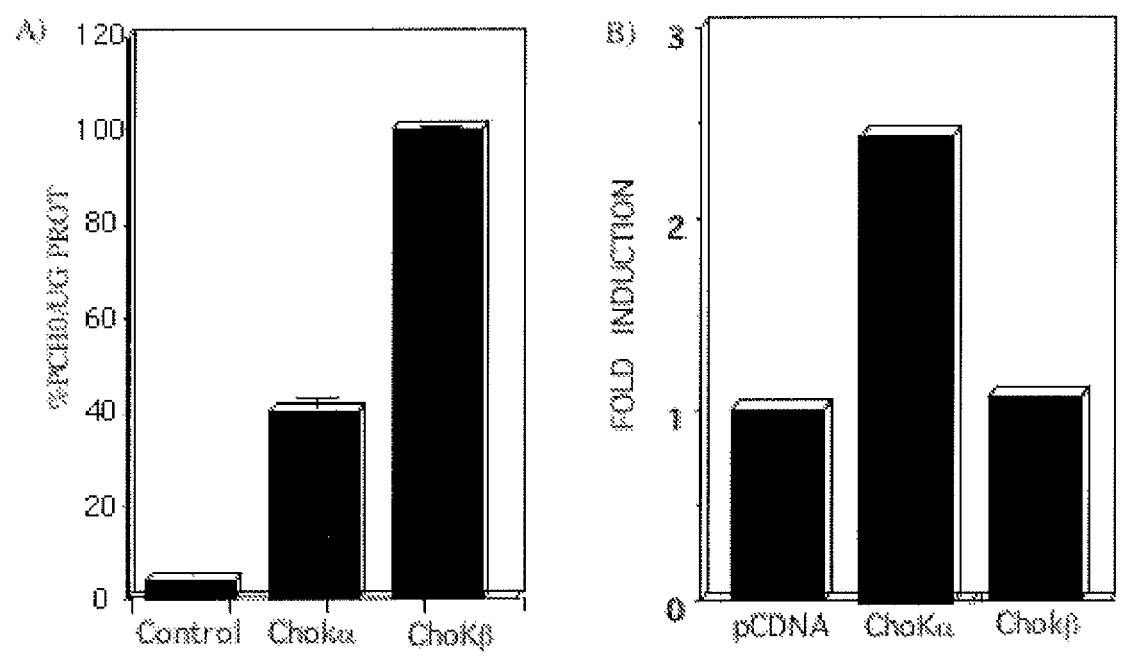
FIG. 1: A) Choline kinase activity (ChoK) in human Hek293T cell (Human embryonic kidney cells) extracts after overexpressing choline kinase alpha and beta (ex vivo choline kinase activity assay). B) Intracellular phosphorylcholine levels in live cells (in vitro choline kinase activity assay).

To facilitate understanding the present patent application, the meaning of some terms and expressions shall be defined below within the context of the invention:

The terms "subject" or "individual" refer to members of mammal animal species and includes but is not limited to domestic animals, primates and humans; the subject is preferably a male or female human being of any age or race.

The term "cancer" refers to the disease that is characterized by an abnormal or uncontrolled growth of cells capable of invading adjacent tissues and spreading to distant organs.

The term "carcinoma" refers to the tissue resulting from the abnormal or uncontrolled cell growth.

The term "breast cancer" or "breast carcinoma" refers to any malignant proliferative mammary cell disorder.

The term "colon cancer" or "colon carcinoma" refers to any malignant proliferative colon cell disorder.

The term "rectal cancer" or "rectal carcinoma" refers to any malignant proliferative rectal cell disorder.

The term "tumor" refers to any abnormal tissue mass resulting from a benign (non-cancerous) or malignant (cancerous) neoplastic process.

The term "gene" refers to a deoxyribonucleotide molecular chain encoding a protein.

The term "DNA" refers to deoxyribonucleic acid. A DNA sequence is a deoxyribonucleotide sequence.

The term "cDNA" refers to a complementary nucleotide sequence of an mRNA sequence.

The term "RNA" refers to ribonucleic acid. An RNA sequence is a ribonucleotide sequence.

The term "mRNA" refers to messenger ribonucleic acid, which is the fraction of total RNA which translates proteins.

The term "mRNA transcribed from" refers to the transcription of the gene (DNA) in mRNA as a first step so that the gene is expressed and translated to a protein.

The term "nucleotide sequence" or "nucleotidic sequence" indistinctly refers to a ribonucleotide (RNA) or a deoxyribonucleotide (DNA) sequence.

The term "protein" refers to a molecular amino acid chain, attached by covalent or non-covalent bonds. The term includes all forms of post-translational modifications, for example glycosylation, phosphorylation or acetylation.

The terms "peptide" and "polypeptide" refer to molecular amino acid chains representing a protein fragment. The terms "protein" and "peptide" are used indistinctly.

The term "antibody" refers to a glycoprotein exhibiting specific binding activity for a target molecule, which is referred to as "antigen". The term "antibody" comprises monoclonal antibodies or polyclonal antibodies, either intact or fragments thereof; and it includes human antibodies, humanized antibodies and antibodies of non-human origin. "Monoclonal antibodies'" are homogenous populations of highly specific antibodies which are directed against a single antigen site or "determinant". "Polyclonal antibodies" include heterogeneous populations of antibodies which are directed against different antigen determinants.

The term "epitope", as it is used in the present invention, refers to an antigen determinant of a protein, which is the amino acid sequence of the protein that a specific antibody recognizes.

The term "therapeutic target" refers to nucleotide or peptide sequences against which a drug or therapeutic compound can be designed and clinically applied.

The term "antagonist" refers to any molecule inhibiting the biological activity of the antagonized molecule. Examples of antagonist molecules include, among others, proteins, peptides, natural peptide sequence variations and small organic molecules (with molecular weight of less than 500 Daltons).

The term "normal reference values" used in the present invention refers to the level of certain proteins, mRNA or other metabolites of the body present in a healthy individual.

The term normal tissue used in the present invention refers to a non-cancerous tissue, including commercial cell cultures.

The present invention is based on the discovery that the choline kinase alpha protein expression increases in tumor processes, and especially in lung, breast and colorectal cancers. As well as on the surprising discovery that the overexpression of said protein induces tumors in vivo and therefore that the inhibition of the expression and/or activity of this enzyme is an excellent method for the treatment of cancer, especially for lung, breast and colorectal cancer. Choline kinase alpha therefore is a good potential therapeutic target in human tumorigenesis.

In this sense, the present invention provides in the first place an in vitro method for detecting the presence of cancer in an individual, preferably lung, breast or colorectal cancer, for determining the stage or severity of said cancer in the individual, or for monitoring the effect of the therapy administered to an individual having said cancer, comprising:
  a) the detection and/or quantification of the choline kinase alpha protein, of the mRNA of the choline Kinase alpha gene or the corresponding cDNA in a sample of said individual, and
  b) the comparison of the amount of choline kinase alpha protein, the amount of mRNA of the choline kinase alpha gene or the amount of the corresponding cDNA detected in a sample of an individual; with the amount of choline kinase alpha protein, with the amount of the mRNA of the choline kinase alpha gene or with the amount of the corresponding cDNA detected in the samples of control individuals or in earlier samples of the same individual or with the normal reference values.

The method provided by the present invention has high sensitivity and specificity, and is based on subjects or individuals diagnosed with cancers, preferably lung, breast and colorectal cancers, having high transcribed mRNA levels of the choline kinase alpha gene, or high concentrations of the protein encoded by the choline kinase alpha gene (choline kinase alpha protein), in comparison with the corresponding levels in samples from subjects with no medical history of these carcinomas. However, the expression in humans of the choline kinase beta gene is not correlated with any of the previously mentioned types of cancer.

The present method comprises a step for obtaining the sample from the individual. Different fluid samples can be worked with, such as for example: urine, blood, plasma, serum, pleural fluid, ascitic fluid, synovial fluid, bile, gastric juice, cerebrospinal fluid, feces, saliva, bronchoscopy sample fluids, etc. The sample can be obtained by any conventional method, preferably surgical resection.

The samples can be obtained from previously diagnosed or not diagnosed subjects, with a certain type of cancer; or also from a subject undergoing treatment, or who has been previously treated for a cancer, particularly for lung, breast or colorectal cancer.

The present method further comprises a sample extraction step, either for obtaining the protein extract from the sample or for obtaining the total RNA extract. One of these two extracts represents the working material for the next phase. The protocols for extracting the total protein or total RNA are well known by the person skilled in the art (Chornczynski P. et al., Anal. Biochem., 1987, 162: 156; Chornczynski P., Biotechniques, 1993, 15: 532; Molina, M. A., et al., Cancer Res., 1999, 59: 4356-4362).

Any conventional assay can be used in the framework of the invention for detecting a cancer, provided that it measures in vitro the transcribed mRNA levels of the choline kinase alpha gene or its complementary cDNA, the concentration of the choline kinase alpha protein in samples collected from the individuals to be analyzed and from control individuals.

Therefore, this invention provides a method for detecting the presence of cancer, especially lung, breast or colorectal cancer, for determining the stage or severity of said cancer in the individual, or for monitoring the effect of the therapy administered to an individual having said cancers, either based on the measurement of the concentration of the choline kinase alpha protein, or on the measurement of the choline kinase alpha gene expression level.

In the event that the intention is to detect the choline kinase alpha protein, the method of the invention comprises a first step for placing the protein extract from the sample into contact with a composition of one or more specific antibodies against one or more epitopes of the choline kinase alpha protein, and a second step for quantifying the complexes formed by antibodies and the choline kinase alpha protein.

There is a wide variety of immunological assays available for detecting and quantifying the formation of specific antigen-antibody complexes; a number of competitive and non-competitive protein binding assays have been previously described, and a large number of these assays are commercially available.

Therefore, the choline kinase alpha protein can be quantified with antibodies such as, for example: monoclonal antibodies, polyclonal antibodies, either intact or fragments thereof, "combi-bodies" and Fab or scFv fragments of antibodies specific against the choline kinase alpha protein; these antibodies being human, humanized or of a non-human origin. The antibodies used in these assays can be marked or unmarked; the unmarked antibodies can be used in agglutination assays; the marked antibodies can be used in a wide variety of assays. The marking molecules that can be used to mark the antibodies include radionucleotides, enzymes, fluorophores, chemiluminescent reagents, enzymatic substrates or cofactors, enzymatic inhibitors, particles, dyes and derivatives.

There is a wide variety of well known assays which can be used in the present invention using non-marked antibodies (primary antibody) and marked antibodies (secondary antibody); these techniques include Western blot, ELISA (Enzyme-Linked Immunosorbent assay), RIA (Radioimmunoassay), competitive EIA (Competitive enzyme immunoassay), DAS-ELISA (Double antibody sandwich-ELISA), immunocytochemical and immunohistochemical techniques, techniques based on the use of protein biochips or microarrays including specific antibodies or assays based on colloidal precipitation in formats such as dipsticks. Other ways of detecting and quantifying the protein EFNB2 or the protein EDNRA include affinity chromatography techniques, ligand binding assays or lectin binding assays.

The preferred immunoassay in the method of the invention is a double antibody sandwich-ELISA (DAS-ELISA) assay. Any antibody or combination of antibodies, specific against one or more epitopes of the choline kinase alpha protein can be used in this immunoassay. As an example of one of the many possible formats of this assay, a monoclonal or polyclonal antibody, or a fragment of this antibody, or a combination of antibodies, which coat a solid phase are placed in contact with the sample to be analyzed and are incubated for a suitable time and in suitable conditions for forming the antigen-antibody complexes. After a washing in suitable conditions to eliminate the non-specific complexes, an indicator reagent, comprising a monoclonal or polyclonal antibody or a fragment of this antibody, or a combination of these antibodies, bonded to a signal generating compound is incubated with the antigen-antibody complexes under suitable conditions and for a suitable time. The presence of the choline kinase alpha protein in the sample to be analyzed is detected and quantified, should it exist, by measuring the generated signal. The amount of choline kinase alpha protein present in the sample to be analyzed is proportional to that signal.

In the event that the intention is to detect the mRNA or cDNA corresponding to the choline kinase alpha gene, and not the proteins they encode, the method of the invention for detecting in vitro carcinoma has various steps. Therefore, once the sample is obtained and the total RNA is extracted, the method of the invention, the detection of mRNA or of the corresponding cDNA of the choline kinase alpha gene, comprises a first step of amplifying the mRNA present in the total RNA extract, or the corresponding cDNA synthesized by reverse transcription of the mRNA, and a second step of quantifying the amplification product of the mRNA or cDNA of the choline kinase alpha gene.

An example of amplifying the mRNA consists of retrotranscribing the mRNA into cDNA (RT), followed by polymerase chain reaction (PCR); PCR is a technique for amplifying a certain nucleotide sequence (target) contained in a mixture of nucleotide sequences. An excess pair of oligonucleotide primers which hybridize with the complementary strands of the target nucleotide sequence is used in the PCR. Then an enzyme with polymerase activity (DNA Taq Polymerase) extends each primer using as a mold the target nucleotide sequence. The extension products are then converted into target sequences after disassociation of the original target strand. New primer molecules hybridize and the polymerase extends them; the cycle is repeated to exponentially increase the number of target sequences. This technique is described in patents U.S. Pat. No. 4,683,195 and U.S. Pat. No. 4,683,202. Many methods for detecting and quantifying PCR amplification products have been previously described and any of them can be used in this invention. In a preferred method of the invention, the amplified product is detected by agarose gel electrophoresis.

In another example, the detection of the mRNA is carried out by transferring the mRNA to a nylon membrane by means of transfer techniques such as for example Northern blot, and detecting it with specific probes of the mRNA or the corresponding cDNA of the choline kinase alpha gene.

In a particular embodiment, the amplification and quantification of the mRNA corresponding to the choline kinase alpha gene is carried out at the same time by means of real-time quantitative RT-PCR (Q-PCR).

The last step of the method of the invention for detecting in vitro the carcinomas in question in a sample from an individual comprises comparing the amount of choline kinase alpha protein, the amount of mRNA of the choline kinase alpha gene or the amount of the corresponding cDNA of the sample from an individual, with the amount of choline kinase alpha protein, the amount of mRNA of the choline kinase alpha gene or the amount of the corresponding cDNA detected in the samples of control subjects or in earlier samples of the same individual, or with the normal reference values.

In a second object, the invention also provides an in vitro method for identifying and evaluating the effectiveness of compounds for cancer therapy; preferably for lung, breast or colorectal cancer, comprising:

a) placing a culture of tumor cells, preferably lung, breast, colon or rectal tumor cells, in contact with the candidate compound, under the suitable conditions and for the suitable time to allow them to interact, b) detecting and quantifying the expression levels of the choline kinase alpha gene or the choline kinase alpha protein, and c) comparing said expression levels with those of the control cultures of tumor cells not treated with the candidate compound.

The quantification of the expression levels of the choline kinase alpha gene or the choline kinase alpha protein is carried out similarly to that indicated in the method of the invention for detecting in vitro the presence of lung, breast or colorectal cancer in an individual.

When an agent reduces the choline kinase alpha gene expression levels or reverses the effects of the high expression of said gene, preferably reducing the cell proliferation levels, this agent becomes a candidate for cancer therapy.

Therefore, another object of the invention refers to the use of nucleotide or peptide sequences derived from the choline kinase alpha gene in methods of finding, identifying, developing and evaluating the effectiveness of compounds for cancer therapy, especially for lung, breast or colorectal cancer. It is essential to point out the importance that has recently been acquired by drug screening methods based on the competitive or non-competitive binding of the potential drug molecule to the therapeutic target.

Another additional object of the invention refers to the use of nucleotide or peptide sequences derived from the choline kinase alpha gene for detecting the presence of cancer, especially lung, breast or colorectal cancer, for determining the stage or severity of said cancers in the individual, or for monitoring the effect of the therapy administered to an individual having any of these cancers.

Another object of the invention consists of providing agents characterized in that they inhibit the expression and/or activity of the choline kinase alpha protein. These agents, which can be identified and evaluated according to the present invention, can be selected from the group formed by:

a) an antibody, or combination of antibodies, specific against one or more epitopes present in the choline kinase alpha protein, preferably a human or humanized monoclonal antibody; also being able to be a fragment of the antibody, a single-chain antibody or an anti-idiotype antibody, b) cytotoxic agents, such as toxins, molecules with radioactive atoms, or chemotherapeutic agents, including but not limited to small organic and inorganic molecules, peptides, phosphopeptides, anti-sense molecules, ribozymes, siRNAs, triple helix molecules, etc., inhibiting the expression and/or activity of the choline kinase alpha protein, and c) antagonist compounds of the choline kinase alpha protein, inhibiting one or more of the functions of the choline kinase alpha protein.

A pharmaceutical composition comprising a therapeutically effective amount of one or several of the previously mentioned agents together with one or more excipients and/or carrier substances also constitutes an object of the present invention. Furthermore, said composition may contain any other active ingredient that does not inhibit the function of the choline kinase alpha protein.

The excipients, carrier substances and auxiliary substances must be pharmaceutically and pharmacologically tolerable, such that they can be combined with other compounds of the formulation or preparation and do not have any adverse effects on the treated organism. The pharmaceutical compositions or formulations include those which are suitable for oral or parenteral administration (including subcutaneous, intradermal, intramuscular and intravenous), although the best administration route depends on the patient's condition. The formulations can be in the form of single doses. The formulations are prepared according to known methods in the field of pharmacology. The amounts of active substances to be administered may vary according to the particularities of the therapy.

A further aspect of the present application consists of a diagnostic kit for carrying out the present invention. Therefore, in a particular embodiment, the present invention includes a kit comprising an antibody especially recognizing the choline kinase alpha protein and a carrier in a suitable container. In another particular embodiment, this kit is used for detecting the presence of cancer in an individual, preferably lung, breast or colorectal cancer, for determining the stage or severity of said cancer in the individual, or for monitoring the effect of the therapy administered to an individual having said cancer.

A final aspect of the present invention consists of an in vitro method for diagnosing the survival time of a patient with breast, lung or bladder cancer comprising the evaluation of the choline kinase alpha protein expression level in a sample of the cancerous tissue extracted from the patient by means of determining in said sample at least one parameter related to the choline kinase alpha protein which is selected from the level of its messenger RNA, the concentration of said protein or the enzymatic activity of said protein, and the comparison of the obtained value with the value corresponding to one or more normal non-cancerous tissue samples.

The following examples illustrate the invention.

Example 1

Choline Kinase Activity of the Isoforms

As is shown in FIG. 1, both enzymes CK$\alpha$2 (52 kDa, 457 amino acids) and CK$\alpha$1 (45 kDa, 395 amino acids) have potent choline kinase activity, determined by their ability to produce phosphorylcholine from choline in the presence of ATP and magnesium (FIG. 1A). This activity is shown in both its recombinant form, expressed in E. Coli, and after the transfection in human HEK293 cells. However, and despite the fact that both enzymes have choline kinase activity, the intracellular levels of phosphorylcholine in live cells are not equally altered, being virtually undetectable in the cells which overexpress choline kinase beta (FIG. 1B). These results suggest that both physiological regulation and biological function of these two proteins, and therefore, their behavior in tumorigenesis, may be differential.

Example 2

Specificity of the Antibody

Figure 2:
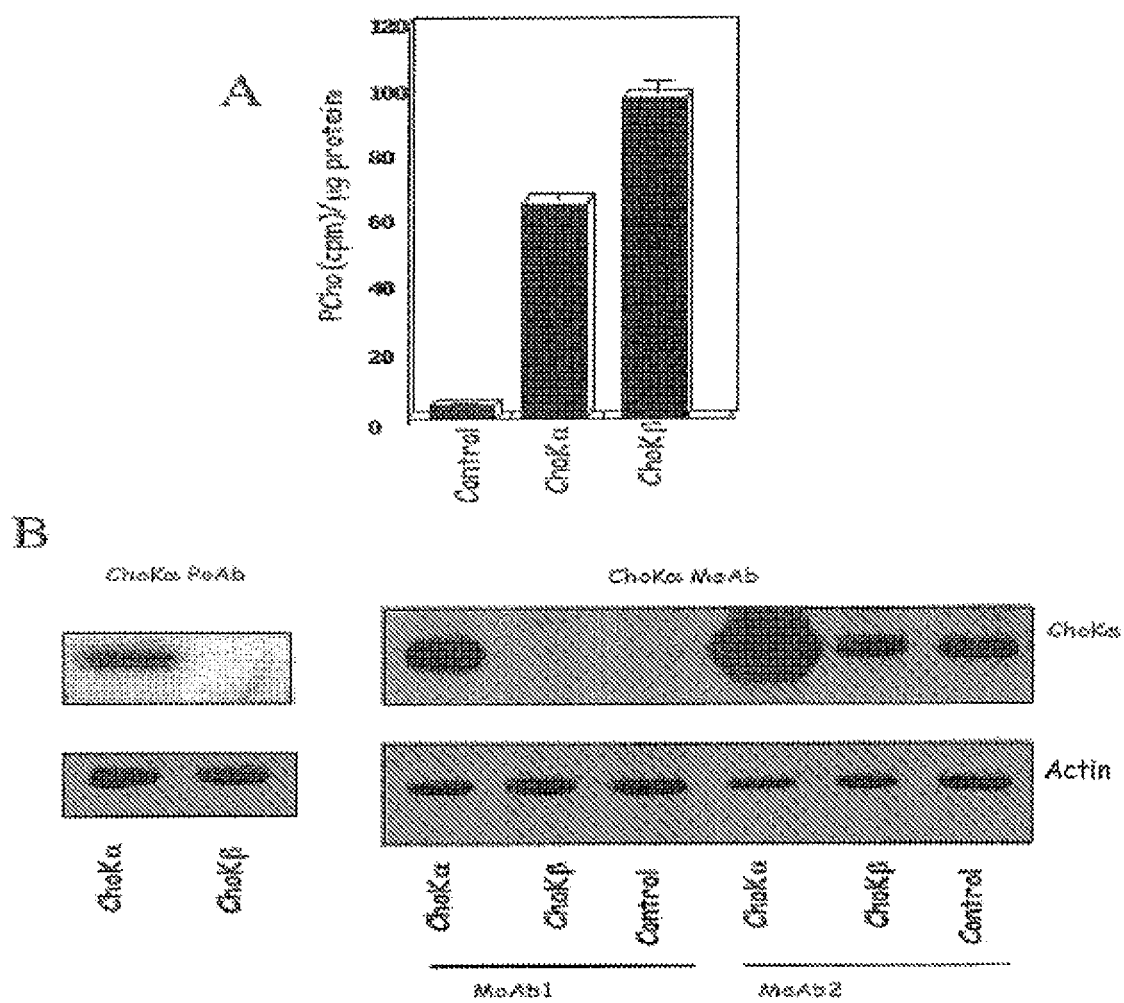
FIG. 2: A) ChoK activity in human Chok293T cells after overexpressing choline kinase alpha and beta. B) Specificity of the monoclonal antibodies generated against choline kinase alpha in the same extracts shown in A.

Polyclonal and monoclonal antibodies recognizing the choline kinase alpha enzyme, a protein which has been semi-purified and expressed as an antigen in generation phase and as production control in the remain phases of the process, have been developed. Despite having been developed against choline kinase alpha, due to the fact that both enzymes (CK$\alpha$ and CK$\beta$) have 65% overall homology throughout their sequence, and in some conserved regions such as the choline binding and catalytic activity domains homology reaches 75%, it is necessary to check which isoenzymes are able to recognize the generated polyclonal and monoclonal antibodies. we have verified that both the polyclonal and monoclonal antibodies used are specific for choline kinase alpha and that they do not recognize choline kinase beta. To that end both choline kinase alpha and beta proteins were overexpressed in human HEK293T cells, and after checking that the two proteins are present and active (FIG. 2A), their analysis was carried out by immunodetection techniques (Western blot) with both the polyclonal antibody with which prior studies were carried out [Ramirez de Molina, A., Gutiérrez, R., Ramos, M. A., Silva, J. M., Silva, J., Sánchez, J. J., Bonilla, F., Lacal, J. C. Oncogene 21, 4317-4322 (2002); Ramirez de Molina, A., Rodriguez-González, A., Gutiérrez, R., Martinez-Piñero, L., Sánchez, J. J., Bonilla, F., Rosell, R., Lacal, J. C. Biochem. Biophys. Res. Commun. 296, 580-583 (2002)], and with the new monoclonal antibodies generated against choline kinase alpha. As is shown in FIG. 2B, which shows an example with two of these antibodies, even by overexpressing choline kinase beta in conditions in which the activity is increased 80 times, none of the antibodies recognizes this isoform, choline kinase alpha being highly recognized in both the same conditions and in the endogenous control levels in all cases. These results indicate that the prior studies of the group in which the polyclonal antibody was used define choline kinase alpha as the isoenzyme overexpressed in cell lines derived from human tumors and in the analyzed tumors themselves.

These results were not expected given that by definition, polyclonal antibodies recognize different epitopes in the molecule and the choline kinases alpha and beta sequences are 65% homologous, in some regions reaching up to 75%, especially in the consensus domain regions where the catalytic region and the substrate and ATP binding region are located.

Example 3

Specificity for Tumors

Alteration of Choline Kinase Alpha in Different Human Tumors

The availability of antibodies with proven specificity against choline kinase alpha has allowed studying the possible alteration in choline kinase alpha expression in some of the most important tumors today in developed countries, such as breast, colon, and lung cancer. To carry out this study, paraffin sections of samples from between 38 and 50 different patients, each of whom had one of these types of cancer, were carried out and choline kinase alpha expression has been analyzed by means of immunohistochemistry (1HQ), a technique which allows detecting and identifying "in situ" biomolecular components which are an integral part of cells and tissues and which can be carried out in an automated manner in the Pathological Anatomy Department of any hospital. In the breast, colon or lung samples of these patients, it was found that:

In all cases, staining of the tumor with the antibody recognizing choline kinase alpha is highly specific, allowing the clear distinction between the tumor tissue and the normal adjacent tissue.

There is no case in which the normal tissue stains.

Figure 3:
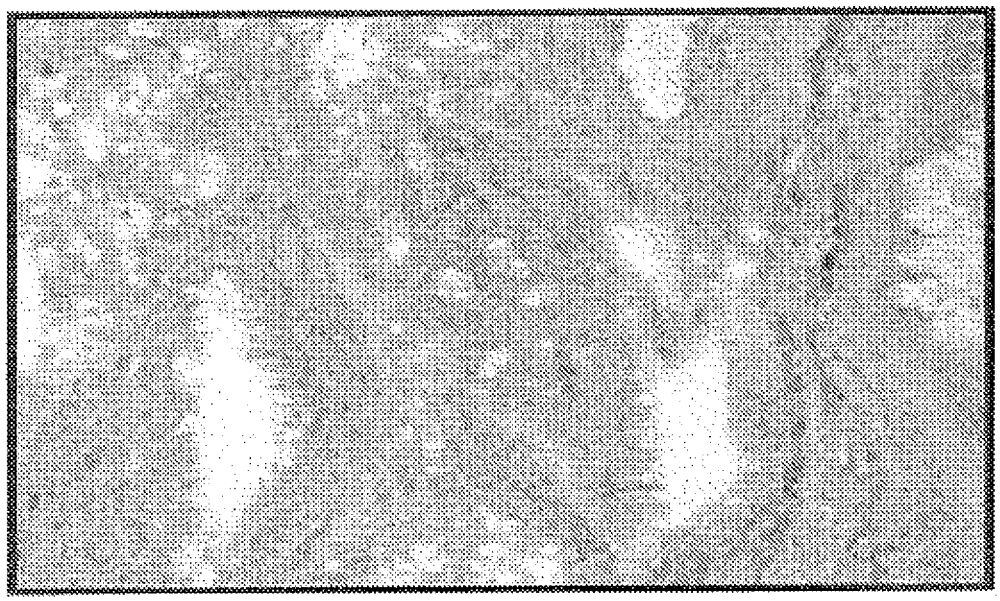
FIG. 3: Choline kinase alpha overexpression determined by means of immunohistochemical techniques in NSCLC (Non-small cell lung cancer).

The choline kinase alpha enzyme is overexpressed with an incidence ranging between 62% and 100% in this type of tumor, demonstrating the high involvement of this isoform, choline kinase alpha, in human tumorigenesis.

in FIG. 3 an example of the results obtained for large cell lung cancer (NSCLC), which today involves 80% of the cases of lung cancer, can be observed. As can be observed, cytoplasmic staining of choline kinase alpha, specific for the tumor nodes and which as previously indicated specifically stains 62% of the samples, occurs.

Figure 4:
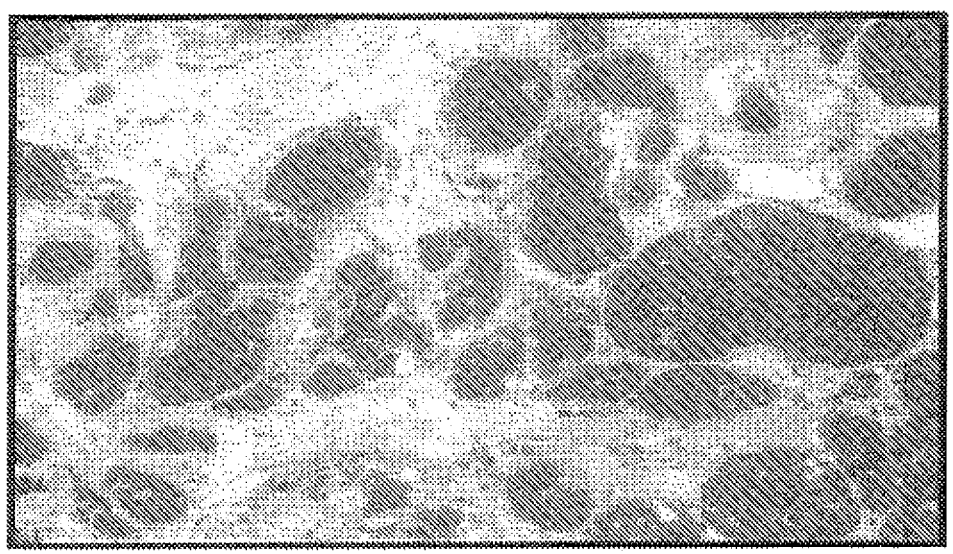
FIG. 4: Choline kinase alpha overexpression determined by means of immunohistochemical techniques in breast cancer.

Following this concept, a similar study has been carried out in 38 patients with breast cancer, the overexpression of choline kinase alpha specifically in tumor tissue in 97% of the cases again being observed (FIG. 4).

Figure 5:
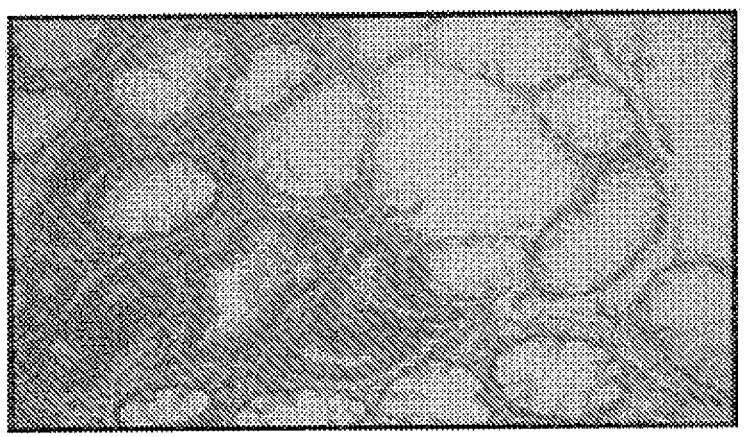
FIG. 5: Choline kinase alpha overexpression determined by means of immunohistochemical techniques in colon cancer. B) Polyp in which the progressive staining is observed from the pre-neoplastic lesions to the mass of the tumor.
Figure 5:

Finally, the study of choline kinase alpha expression in colon cancer has also been carried out, for which purpose paraffin sections of 40 samples from different patients with colon cancer with over 4 years of follow-up have been carried out. The analysis began with carcinomas in situ in stages I, II, III and IV. Similar to the previous case, the normal tissue of each preparation adjacent to the tumor tissue has been used as normal tissue. Positive staining in the normal tissues was not obtained in any case in any of the 40 samples, confirming the high specificity of choline kinase alpha staining in the tumor tissue, in which overexpression of the enzyme was again observed in all cases (FIG. 5A). These results support the high involvement of this isoform of this enzyme in colon cancer. Furthermore, this result led to the analysis of pre-neoplastic lesions, ACFs and polyps with different degrees of dysplasia, in which the results clearly show that choline kinase alpha overexpression is an early event in the colon tissue tumor process which occurs as of the time of dysplasia, suggesting its potential behavior as a "gate-keeper" gene in these tumors and therefore its relevance as a potential new therapeutic target. FIG. 5B shows a polyp in which it can be seen how the staining in the normal tissue is virtually undetectable, and as the dysplasia begins to occur (binuclear cells) the staining increases, becoming more intense in the mass of the tumor.

Example 4

Specificity for Tumors

Oncogenic Behavior of the Choline Kinase Alpha Enzyme

Figure 6:
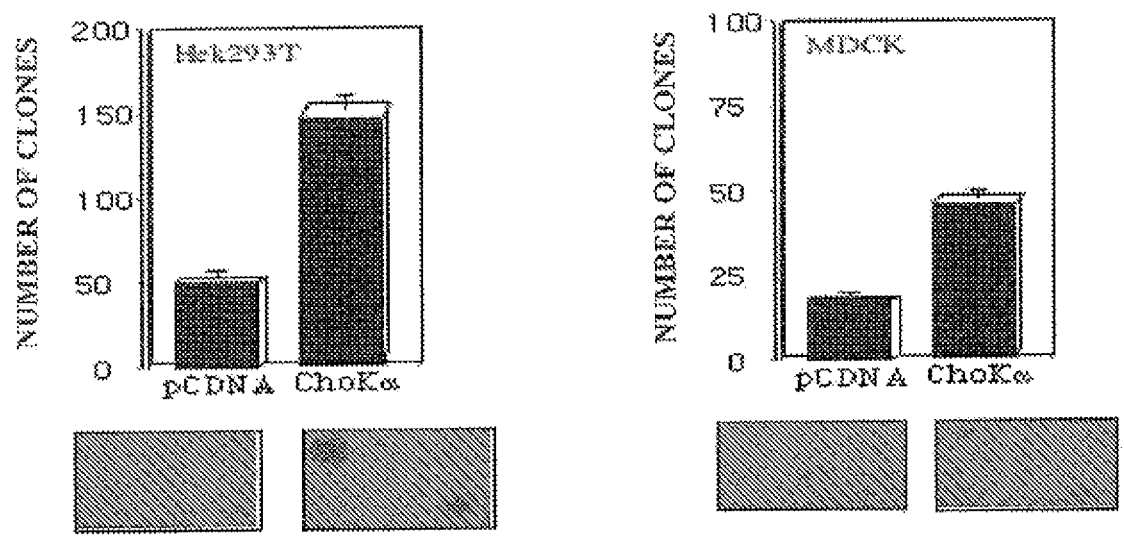
FIG. 6: Attachment-independent growth of cells overexpressing human choline kinase alpha. Both the number of colonies generated and the relative size thereof in the two cell lines analyzed, Hek293 and MDCK, are shown.

Given the very high incidence of dysregulation of choline kinase alpha in some of the most important human tumors today, a study was carried out to determine if this protein alone has oncogenic ability, i.e. if choline kinase alpha has oncogenic activity. To carry out this study, it was first studied if this gene confers growth capacity in an attachment-independent medium, which involves measuring its transforming capacity. Human HEK293T cells were transfected with an empty vector as control and with a choline kinase alpha expression vector, and were seeded in soft agar. As can be seen in FIG. 6, the overexpression of this protein is enough to induce oncogenic transformation of both human HEK293T cells and of epithelial dog MDCK cells.

Figure 7:
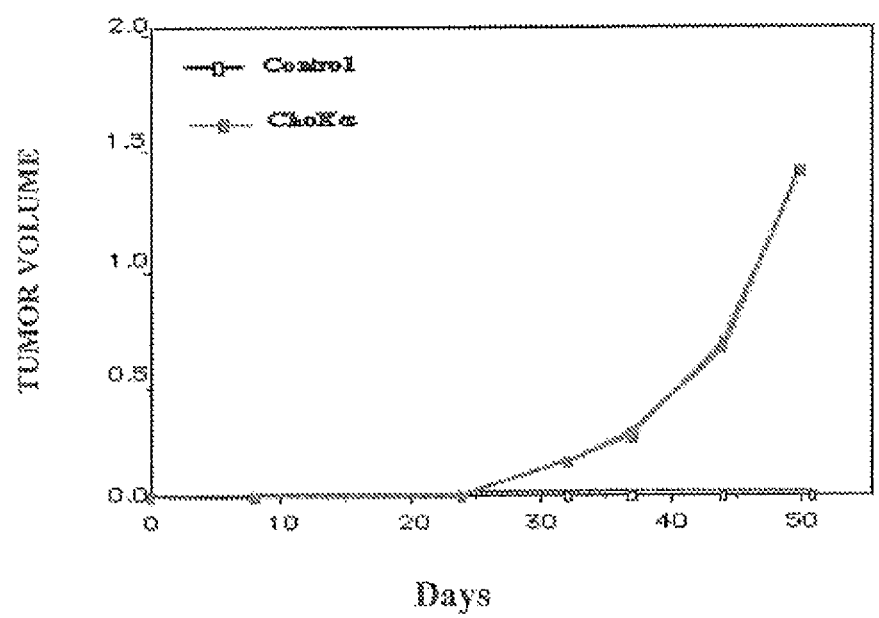
FIG. 7: In vivo oncogenic activity of choline kinase alpha in Nu/Nu mice.
Figure 8:
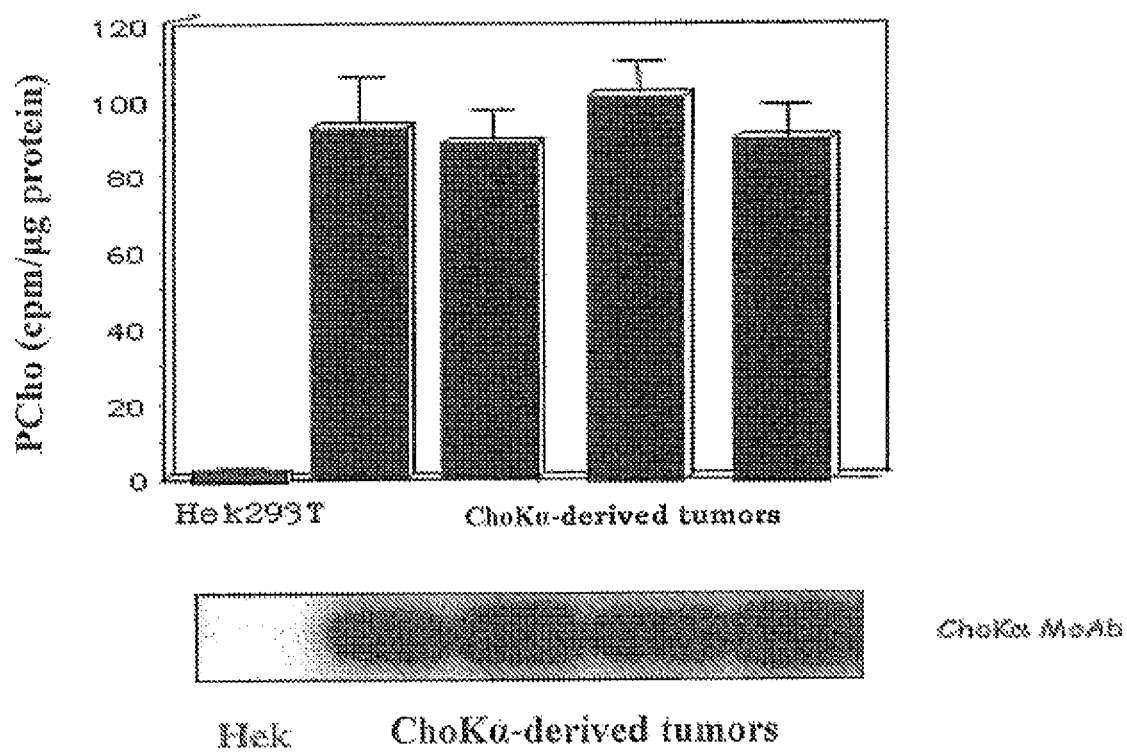
FIG. 8: Expression and enzymatic activity of choline kinase alpha in tumors induced in vivo.

Given that choline kinase alpha has transforming activity in human HEK293T cells, their oncogenic potential was analyzed in vivo. To that end, immunodepressed mice (Nu/Nu) were injected with a million human HEK293T cells which overexpressed either the empty vector as a control, or the choline kinase alpha expression vector. Tumor growth was monitored at least twice a week for 50 days after the injection. While the control cells did not induce any tumor in any of the injected mice, the cells which overexpressed choline kinase alpha induced tumors in 8 of the 30 injected mice (26%), which reached a mean of 0.6 $cm^3$ after 45 days (FIG. 7). These results show that choline kinase alpha overexpression is enough to induce tumors in vivo, and therefore is a good potential therapeutic target in human tumorigenesis. To verify if the tumors generated by choline kinase alpha maintained their increased expression and activity, the tumors were surgically extracted, lysated and the activity and expression levels of this enzyme were determined with respect to those levels of its parent HEK293T cells as control. As can be seen in FIG. 8, all the analyzed tumors maintain high expression and enzymatic activity levels in a manner similar to that which was obtained before inoculation, showing that choline kinase alpha overexpression induces tumorigenesis in vivo.

Example 5

Pharmacological Specificity

Figure 9:
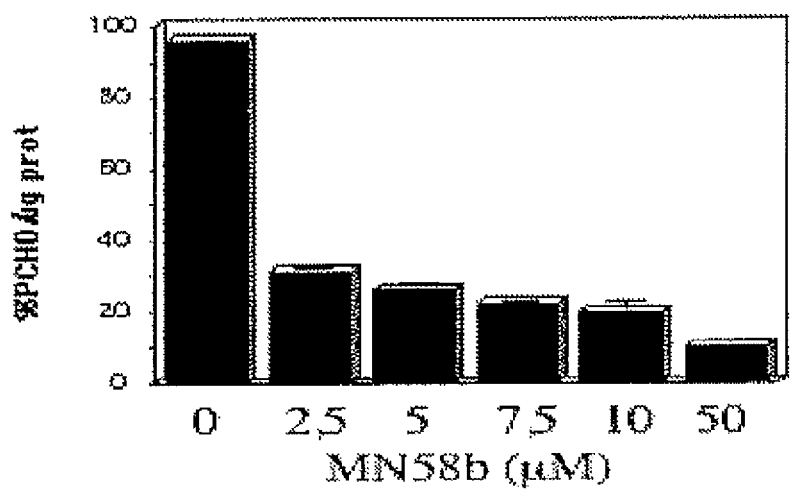
FIG. 9: Specificity of the inhibitor MN58b on choline kinase alpha. E. coli extracts in which recombinant human choline kinase alpha or choline kinase beta proteins are expressed were analyzed in the absence (0) or in the presence of increasing concentrations of MN58b.
Figure 9:
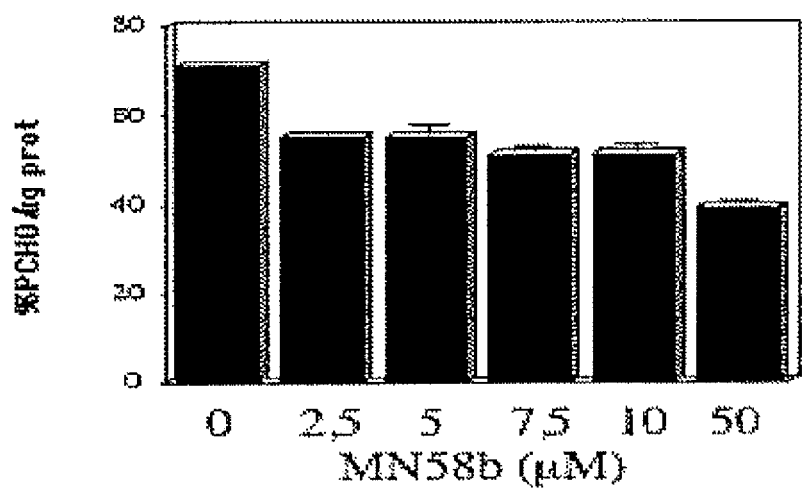

Once the oncogenic activity of the choline kinase alpha isoform, as well as its high incidence of overexpression in human tumors was verified, it was then studied if the antitumor effect of the inhibitor MN58b [Hernández-Alcoceba, R., Saniger, L., Campos, J., Núñez, M. C., Khaless, F., Gallo, M. Á., Espinosa, A., Lacal, J. C. *Oncogene,* 15, 2289-2301 (1997); Hernández-Alcoceba, R., Fernández, F., Lacal J. C. *Cancer Res.* 59, 3112-3118 (1999); Ramirez de Molina A., Bañez-Coronel M., Gutiérrez R., Rodriguez González A., Olmeda D., Megias D., Lacal J. C. *Cancer Res.* 64:6732-6739 (2004)] is specific for this choline kinase alpha isoform or if, in contrast, it could also be attributed to its possible interaction with the choline kinase beta isoform. This verification is necessary because the two choline kinase alpha and choline kinase beta isoforms share up to 75% homology in the substrate binding domains and in the catalytic region. To that end, the two choline kinase isoforms (CKα and CKβ) were expressed in the strain of *E. Coli* bacteria, which lack choline kinase activity, and therefore any enzymatic activity observed is exclusively due to the recombinantly expressed choline kinase isoform. As can be seen in FIG. 9, the enzymatic activity of choline kinase alpha is affected by treatment with MN58b, with a more pronounced effect than the effect exerted by the same inhibitor on the β isoform. In fact, MN58b is 20 times more active against choline kinase alpha that it is against choline kinase beta.

Figure 10:
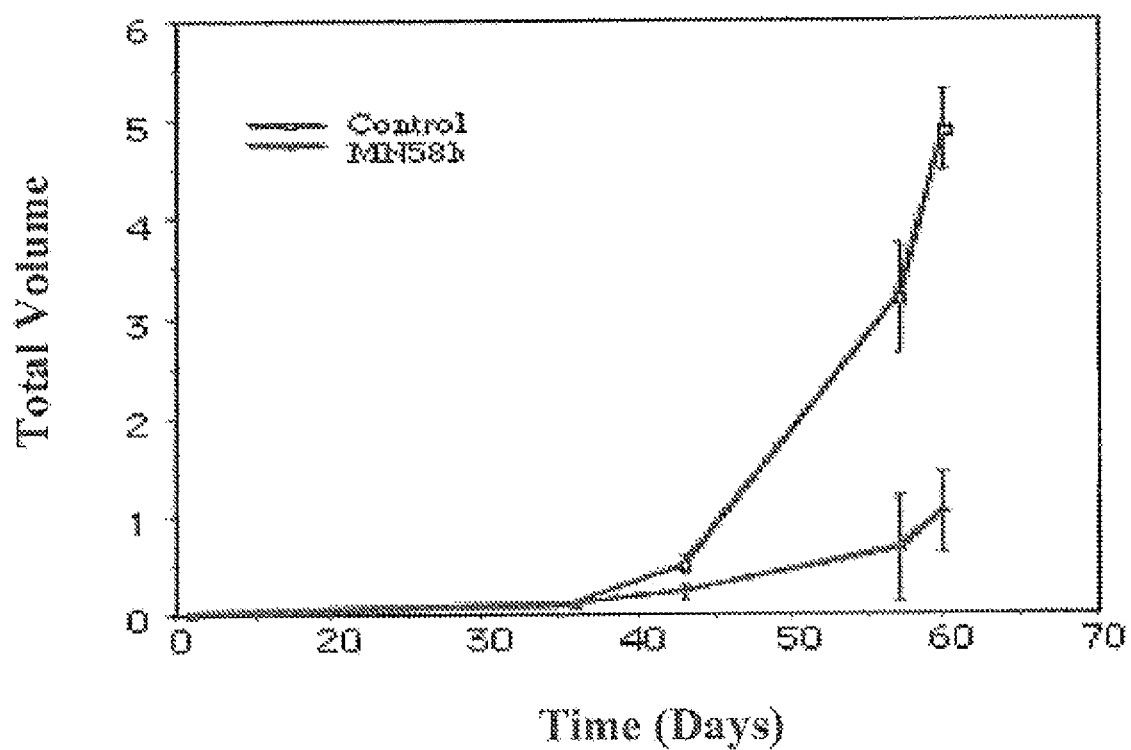
FIG. 10: Anti-tumor effect of the inhibitor MN58b on tumors induced by choline kinase alpha overexpression

Given that tumors have been generated in vivo by overexpressing choline kinase alpha and that MN58b is specific for this isoform, it has been verified if the growth of the tumors induced by ChoKα is susceptible to inhibition by MN58b. To that end, a million human HEK293T cells transfected with the ckα gene which showed a high overexpression of the choline kinase alpha enzyme were subcutaneously injected in immunodepressed Nu/Nu mice. When the tumors reached a tumor volume of 0.1 cm$^3$, treatment with the specific choline kinase alpha inhibitor, MN58b, began, which was administered intraperitoneally in sterile physiological serum for 5 consecutive days with 9 days of rest at a dose of 5 mg/Kg. The control mice received equivalent carrier doses, following the same calendar and the tumors were monitored at least twice a week. As shown in FIG. 10, choline kinase alpha inhibition results in a strong inhibition of tumor growth, reaching 80% tumor growth reduction. These results show that not only is choline kinase alpha overexpression enough to induce tumors in vivo, but the proliferation of tumor cells depends on choline kinase alpha activity.

Example 6

Genetic Specificity

Figure 11:
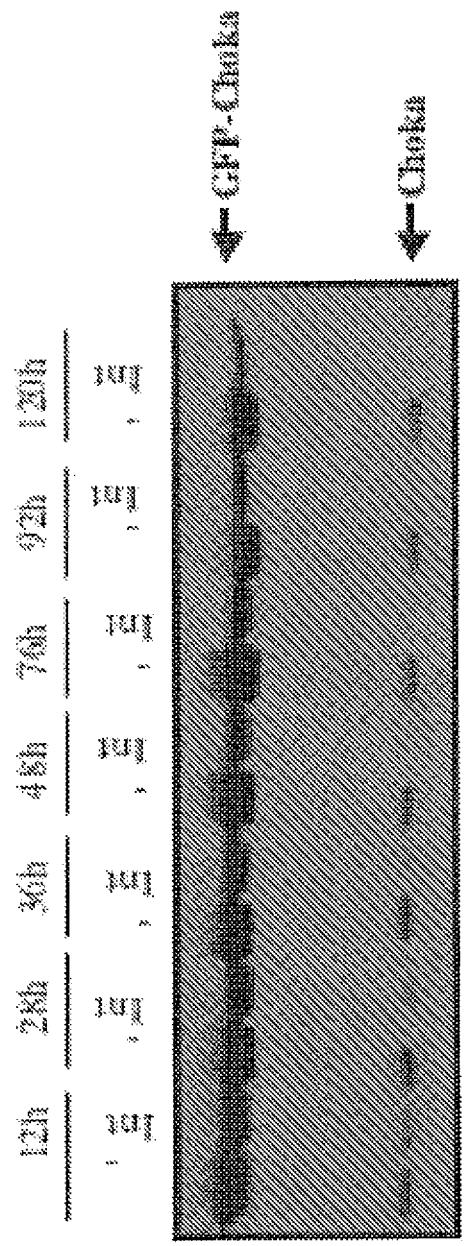
FIG. 11: Blocking of choline kinase alpha expression by the siRNA technique in human HeK293T cells.

All these results support the potential of choline kinase alpha as a new therapeutic target for the design of a new anti-tumor strategy. However, chemical inhibitors can carry out their antiproliferative action by means of effects that are concealed from the investigator, even though they are designed specifically against a certain enzyme, as is the case of the inhibitor MN58b. There are a number of cases in the literature in which it is shown that inhibitors designed specifically against a kinase also affect other kinases which are not even closely related to one another. There is an approach recently developed in the past few years that allows more precisely establishing the effects of interference with a particular enzyme by means of the use of siRNA (small interference RNA) which are capable of precisely and selectively eliminating mRNA for a certain protein without affecting the remaining cell proteins. In this case it was verified that pharmacological interference by means of the use of the inhibitor MN58b, specific against choline kinase alpha, has confirmation at the genetic level by means of the specific inhibition of choline kinase alpha by the siRNA technique. This technique would allow definitively validating ChoKα as a new therapeutic target in cancer. For this purpose, an oligonucleotide capable of hybridizing with the choline kinase alpha messenger RNA (which has been called siCHKA), and therefore capable of specifically blocking expression of this protein, was generated. It was first verified that this siRNA efficiently blocks choline kinase alpha expression in human HEK293T cells, both the endogenous protein and a ChoKα fused to GST and transfected in the same cells (FIG. 11).

Figure 12:
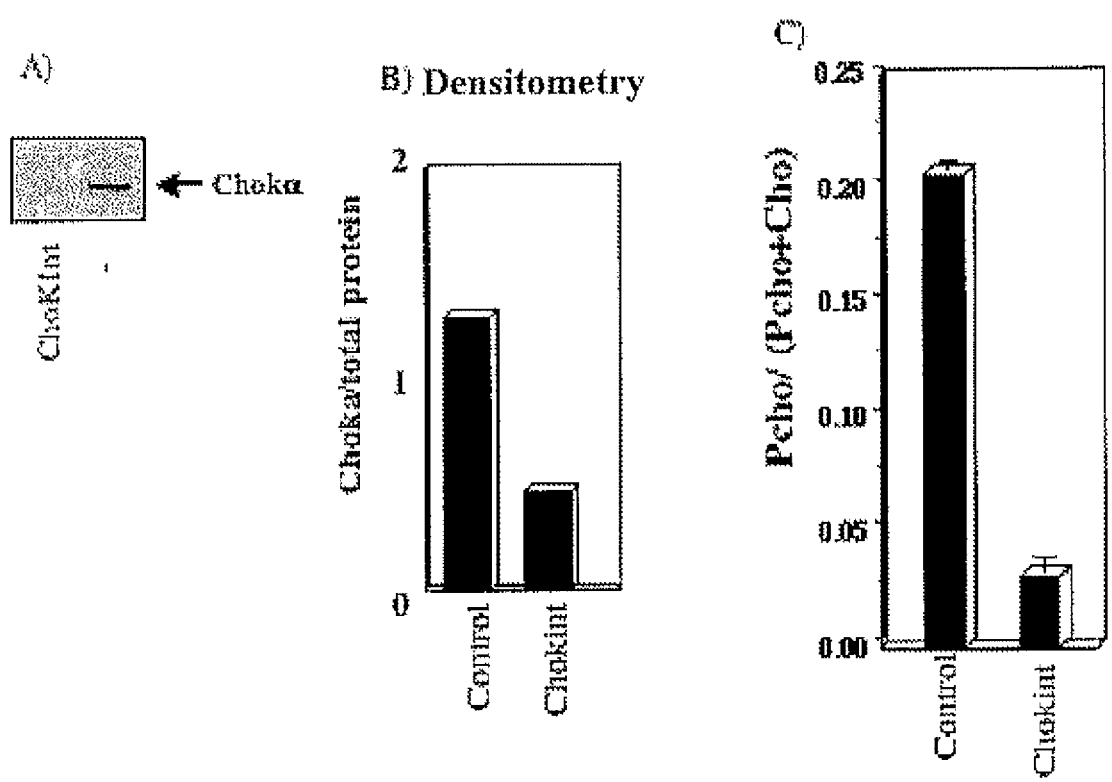
FIG. 12: Blocking of choline kinase alpha expression by means of siRNA in tumor cells derived from a human breast carcinoma, determined both by Western Blotting A) and B) and by enzymatic activity C).
Figure 13:
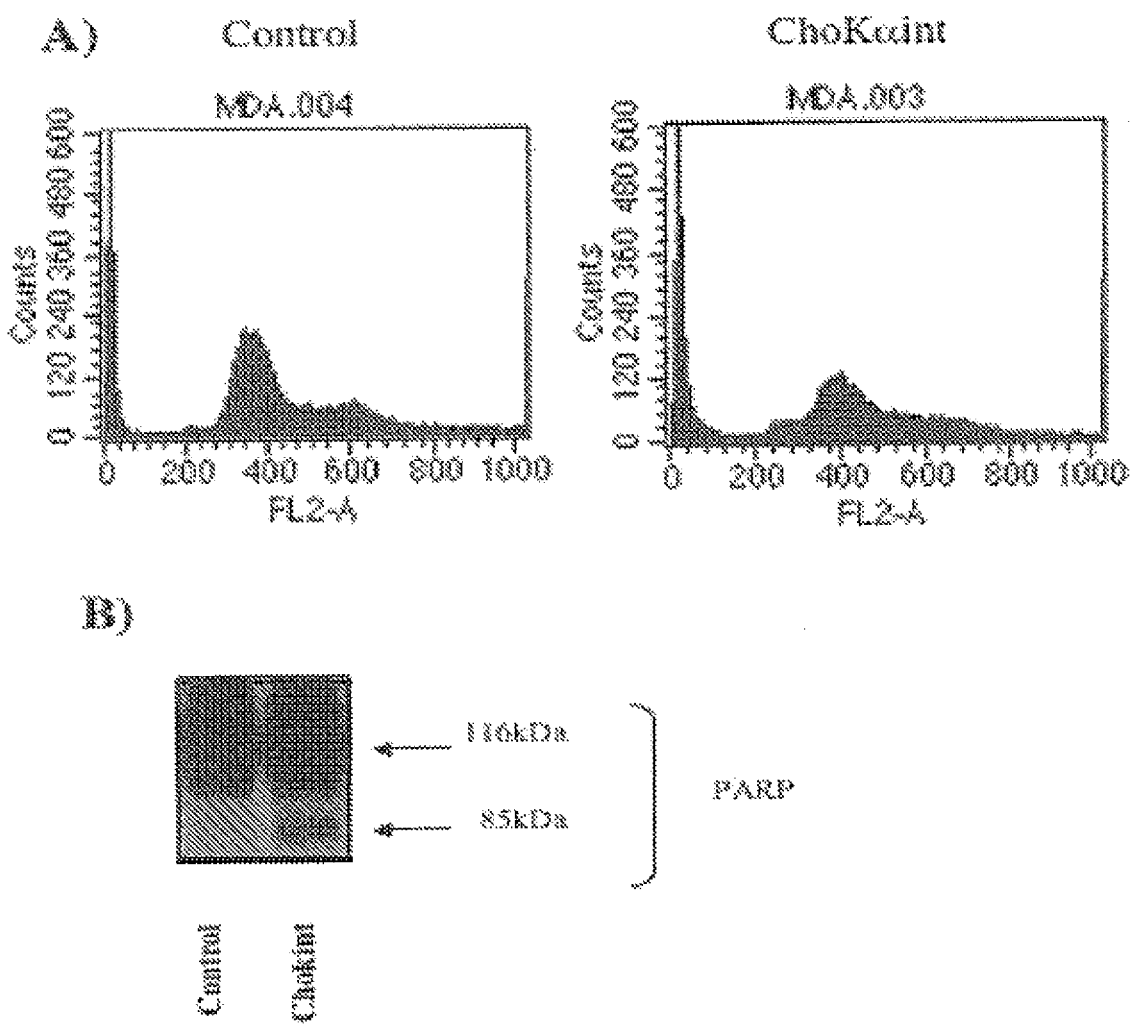
FIG. 13: Death due to apoptosis induced by specific interference RNA of choline kinase alpha in human breast tumor cells MDA-MB-231. A) Flow cytometry analysis with propidium iodide. B) Digestion of PARP associated to death due to apoptosis.

Once it was verified that this interference RNA specific to choline kinase alpha is truly capable of efficiently blocking the expression of this protein, its effect in the tumor cells derived from a human breast carcinoma, MIDA-MI3-231, in which it was previously described that the pharmacological inhibition of choline kinase with MN58b induced a strong anti-tumor effect due to apoptosis induction, was then verified. As can be seen in FIG. 12, despite the lower transfection efficiency obtained in these cells, it was observed that the transfection of siCHKA in MDA-MB-231 implies inhibition of both choline kinase alpha expression and of its enzymatic activity. To verify that the effect of genetic inhibition of choline kinase alpha by means of siRNA is similar to that obtained by means of pharmacological inhibition with MN58b, thus unequivocally demonstrating the specificity of the effect on choline kinase alpha, cell viability after transfection with interference siCHKA was determined. As occurs after treatment of the tumor cells with MN58b, a reduction in cell viability is observed associated to death due to apoptosis which is specific for the cells transfected with the choline kinase alpha interference agent (FIG. 13).

Figure 14:
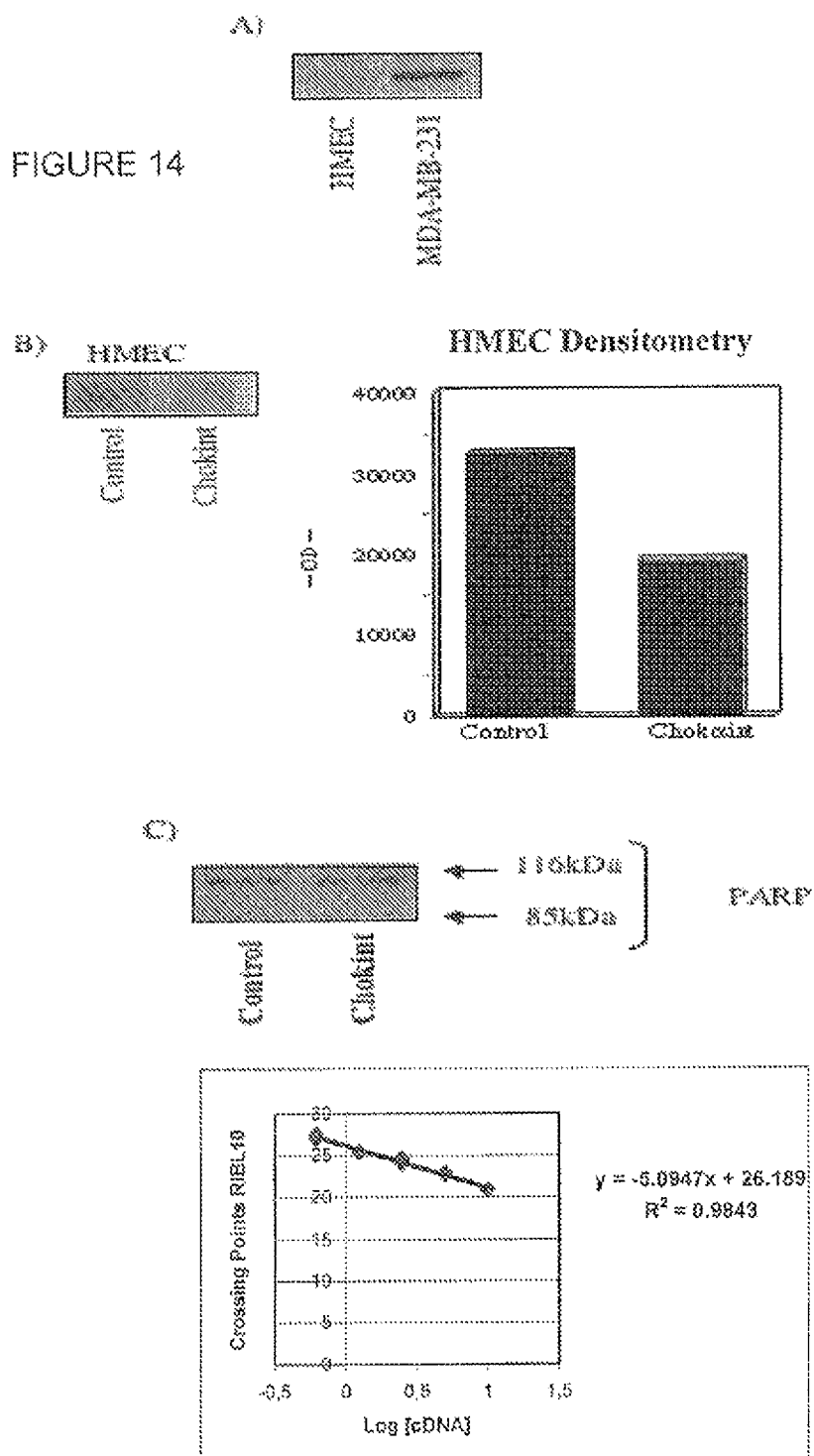
FIG. 14: specific interference RNA of choline kinase alpha in primary human mammary epithelial cells HMEC. A) Basal choline kinase alpha expression levels in normal HMEC cells with respect to the tumor cells MDA-MB-231. B) Interference with choline kinase alpha in HMEC. C) The interference of choline kinase alpha does not induce cell death in primary human HMEC cells.

Finally, as occurs with RMN58b, it was verified that the expression of interference siCHKA, specific for choline kinase alpha, has no effect on the viability of normal primary human mammary cells HMEC (human mammary epithelial cells). In these cells, baseline expression of this protein is very low given that, as previously described, the tumor cells constitutively overexpress choline kinase alpha. However, despite this low baseline expression of choline kinase alpha in the primary cells HMEC, clear interference of the expression of the choline kinase alpha enzyme is obtained, and it can be observed how these cells, unlike what occurs in the tumor cells, do not die due to apoptosis, but they are cycle-arrested (FIG. 14), a result which is identical to that observed in the same cells treated with the inhibitor PAN58b [Rodriguez-González A., Ramirez de Molina A, Fernández F., Ramos M. A., Nuñez, M. del C., Campos, J. M, Lacal J. C. *Oncogene* 22:8803-8812 (2003); Rodriguez-González A, Ramirez de Molina A, Fernández F., Lacal J C. Oncogene 23:8247-8259 (2004); Rodriguez-González A., Ramirez de Molina A., Bañez-Coronel M., Megias D., Núñez M. C and Lacal J. C Int. J. Oncol 26:999-1008 (2005)].

Example 7

Effect of Choline Kinase α on Breast Cancer

Incidence in Survival

In order to have quantitative data confirming the involvement of choline kinase α in the generation and evolution of tumors, additional assays quantifying their expression in patients with the types of cancer with which choline kinase α seems to be specifically related (breast, lung and bladder cancer) and their possible relationship with the prognosis of the evolution of said patient were carried out.

On one hand quantitative analysis of choline kinase α expression was carried out by isolating messenger RNA from patient samples. To that end, automated real-time quantitative PCR reactions were carried out with specific Taqman probes which only recognize the messenger RNA object of study, the messenger RNA corresponding to ChoKα. The obtained data is represented in base 10 logarithmic scale with respect to a control sample of normal tissue.

In the case of data obtained in relation to breast cancer, the obtained results are shown in FIG. 15a. It can be observed that the samples with levels above the median ChoKα activation correspond to those patients with a worse prognosis (presence of lymphatic nodes, development of metastasis, lower survival). This data is confirmed with the data in FIGS. 15b and 15c. In FIG. 15b, prepared with the data obtained in 63 patients with breast cancer, it can be observed how the mean value of ChoKα expression (calculated as relative expression units of the gene, calculated from the mRNA level with the $2^{-\Delta\Delta ct}$ method (Livak, K. J. and Schmitttgen, T. D. (2001) Analysis of relative gene expression data using real-time quantitative PCR and the 2(−Delta Delta C(T)) Method. Methods 25, 402-408)) is much higher in patients presenting metastasis in comparison with those patients who do not. If the probability of survival of these patients is represented according to the presence of lymphatic nodes, which is significantly associated to an increase in ChoKα expression with respect to the controls (p<0.001), it can be observed in a classic Kaplan Meier curve (Kaplan E L, Meier P, Nonparametric estimation from incomplete observations. J. Am. Stat. Assoc., 53:457-481 (1958)) how the probability of survival significantly decreases as the presence of positive lymphatic nodes increases (p=0.046) (FIG. 15c), the same trend being observed when patient survival is represented according to ChoKα expression (p=0.059).

Example 8

Effect of Choline Kinase α in Lung Cancer

Overexpression Level and Incidence in Survival

Several tests were carried out to complement the study on the importance of choline kinase α overexpression in lung cancer.

Figure 16A:
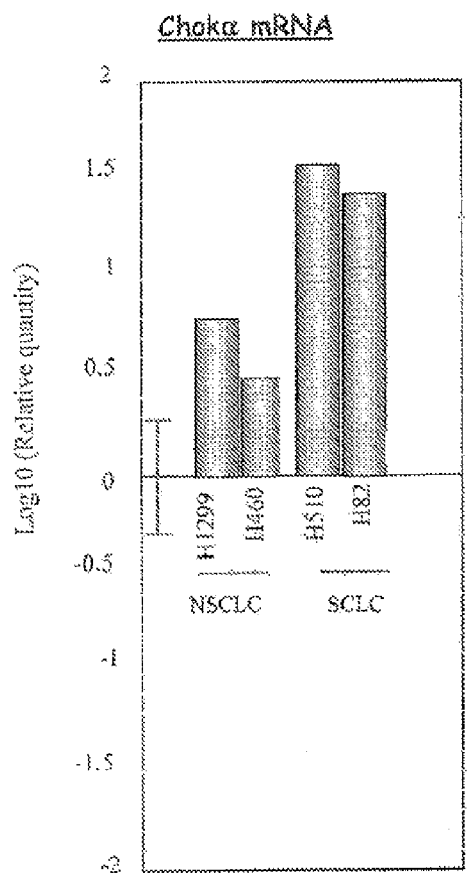
FIG. 16a: choline kinase alpha messenger RNA in cell lines derived from NSCLC (H1299 and H460) or SCLC (H510 and H82) type cancer, detected by real-time quantitative PCR, represented as the base 10 logarithm of the ratio between the amount detected and the amount present in normal primary bronchial epithelial cells (BEC).
Figure 16B:
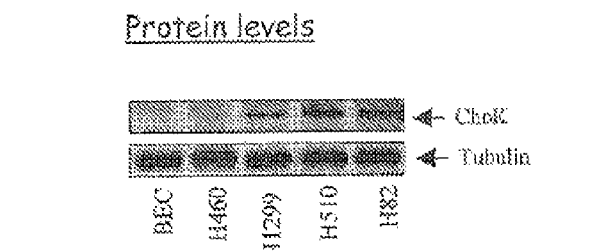
Figure 16C:
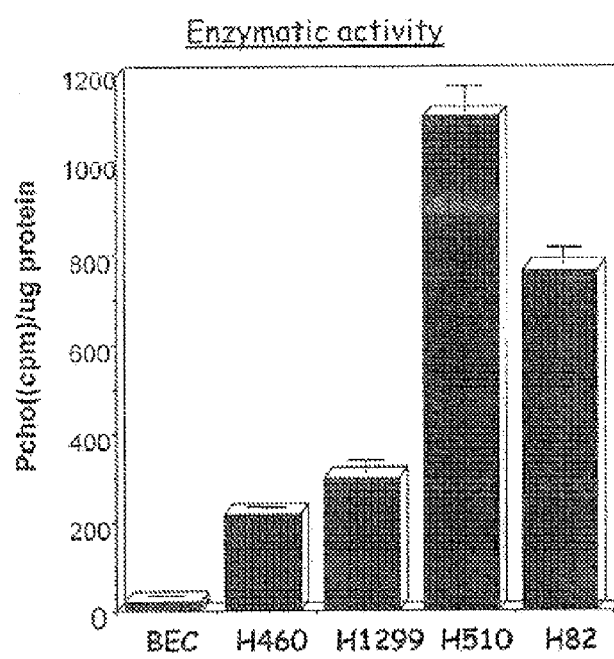
FIG. 16c: choline kinase activity represented by the radioactively marked PCho signal, detected per microgram of protein after 30 minutes, generated from choline marked in each of the cell lines indicated under the corresponding bars.

First, the mRNA levels corresponding to said enzyme in cell lines derived from patients with lung cancer were detected again by means of automated real-time quantitative PCR reactions with specific Taqman probes. They were carried out both on cell lines corresponding to the most common type of lung cancer (75-85%), non-microcytic or NSCLC (non small cell lung cancer), represented by lines H460 and H1299, and on lines corresponding to the other type of cancer, microcytic or SCLC (small cell lung cancer), represented by lines H510 and H82, the data being represented in logarithmic scale relating to normal primary human bronchial epithelial cells, BEC. The results are shown in FIG. 16a. This data was complemented with the data on the detection of protein levels in each of these cell lines by means of immunoassay with a monoclonal antibody (FIG. 16b) and the data on the detectable enzymatic activity in the same lines by measuring the radioactively marked product (PCho) generated after 30 minutes from the marked substrate (Cho) (FIG. 16c). An increase with respect to the controls, which is particularly considerable in the case of the SCLC lines, especially H510, is observed in all cases.

The antiproliferative effect of ChoK inhibition in said cell lines caused by the addition of MN58b was also checked, obtaining the results shown in the following Table, in which the numbers between parentheses indicate the sensitivity of each cell compared with the primary cells. The differences between the primary cells and the four cell lines derived from tumors were significant (p:<0.001) in all the analyzed time periods.

TABLE 1

Antiproliferative effect of ChoK inhibition against cell lines derived from human lung tumors

|  | Cell line | 48 h IC50 (μM) | 72 h IC50 (μM) | 114 h IC50 (μM) |
|---|---|---|---|---|
| Primary | BEC | 40.5 ± 6.2 | 18.3 ± 4.8 | 4.2 ± 0.8 |
| Primary | HMEC | 44.7 ± 4.95 | 20.9 ± 2.7 | 3.4 ± 0.13 |
| NSCLC | H1299 | 10.3 ± 2.5 (4) | 2.7 ± 0.7 (4) | 0.9 ± 0.1 (4) |
| NSCLC | H460 | 7.03 ± 2.03 (6) | 2.6 ± 0.8 (8) | 1.1 ± 0.1 (3) |
| SCLC | H510 | 1.1 ± 0.1 (41) | 0.4 + 0.05 (53) | 0.1 + 0.03 (27) |
| SCLC | H82 | 1.9 ± 0.2 (24) | 0.8 ± 0.04 (27) | 0.27 ± 0.01 (12) |

Figure 17:
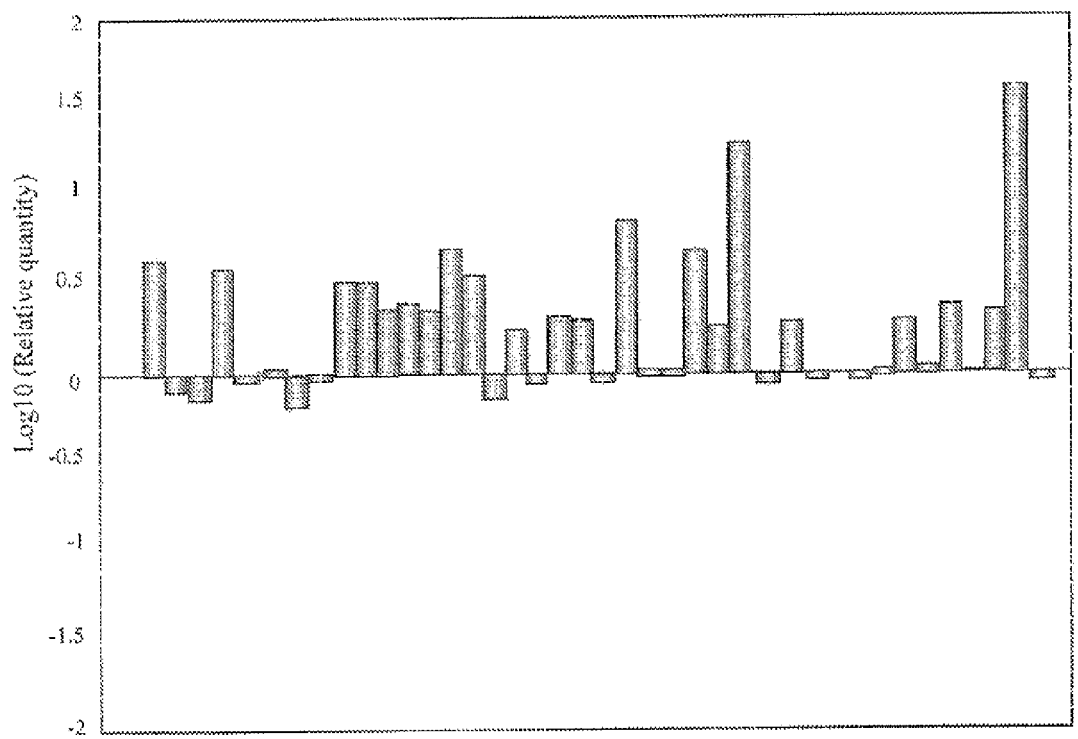
FIG. 17: Choline kinase alpha messenger RNA expression in tissue of tumors extracted from patients with lung cancer NSCLC in early stages, detected by real-time quantitative PCR, represented as base 10 logarithm of the ratio between the amount detected and the amount present in a normal tissue sample.

These results were complemented with ChoKα overexpression studies in human tumor samples from patients with lung cancer, specifically in tissue from patients with NSCLC from whom the tumor was extracted in an early stage. FIG. 17 shows the results obtained in the real-time quantitative PCR analysis of the messenger RNA corresponding to ChoKα in said patients who were operated on in early stages, results which show that in such an early stage of the disease, ChoKα is already overexpressed with respect to normal tissue in 53% of the cases. Again, when the relationship between ChoKα expression and the severity of the cancer (stage and presence or absence of metastasis) is analyzed, it was observed that high ChoKα expression is associated to higher tumor malignancy, as shown in Table 2:

TABLE 2

ChoKα overexpression according to the severity of the lung cancer

|  |  | ChoKα | | |
|---|---|---|---|---|
|  |  | No. and % of patients with normal levels | No. and % of patients with overexpression | p |
| Stage | IA-IIIA[a] | 18 (60%) | 12 (40%) | 0.019 |
|  | IIIB-IV[b] | 0 (0%) | 6 (100%) |  |
| Metastasis | No | 18 (69.2%) | 8 (30.8%) | 0.0015 |
|  | Yes | 0 (0%) | 7 (100%) |  |

Figure 18:
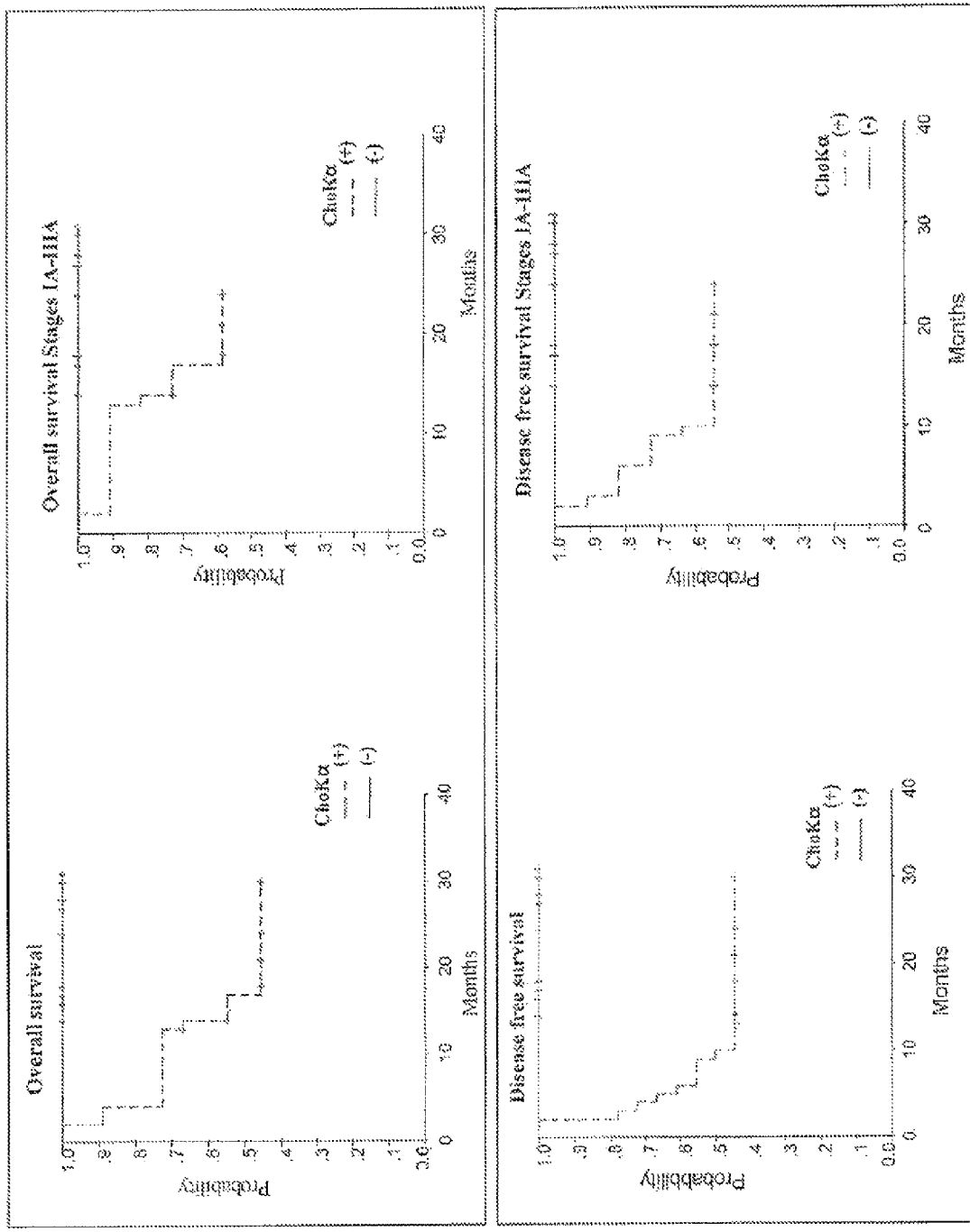
FIG. 18: Evolution of the probability of survival of patients with lung cancer over time, represented in months, in the event that choline kinase alpha expression is detected (dashed lines, ‡) or not detected (continuous lines, †). The overall survival of patients in stages I to IV (graph located in the upper left part), disease-free survival of patients in stages I to IV (time elapsing from when the patients are operated on until they have a relapse) (graph located in the lower left part), survival in the case of cancer in stages IA-IIIA (graph located in the upper right part) and disease-free survival in the case of stages IA-IIIA (graph located in the lower right part).

[a]Stages in which the tumor is small, there is little or no involvement of nodes and no presence of metastasis
[b]Stages with larger tumors with involvement of the nodes and presence of metastasis As in the case of breast cancer, in initial stages of NSCLC ChoKα overexpression in lung cancer is associated to a worse prognosis, as can be observed in the graphs shown in FIG. 18. It can be seen in such figures how the probability of survival is maintained at value 1 over time in those patients in whom direct ChoKα expression is not detected, whereas in those patients in whom ChoKα overexpression is detected, the probability decreases, showing a median value of 9 months when the disease-free survival is evaluated, i.e. the time elapsing from when the patients are operated on until they experience relapse.

Example 9

Effect of Choline Kinase α on Bladder Cancer

Overexpression Level and Incidence on Survival

Figure 19A:
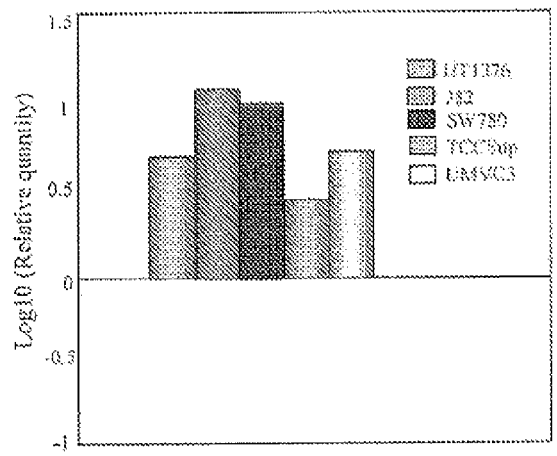
FIG. 19a: Choline kinase alpha messenger RNA in cell lines derived from bladder cancer detected by real-time quantitative PCR, represented as base 10 logarithm 10 of the ratio between the amount detected and the amount present in normal immortalized bladder UrotSa cells; from left to right, the bars correspond to lines HT1376, J82, SW780, TCCSup and UMVC3.
Figure 19B:
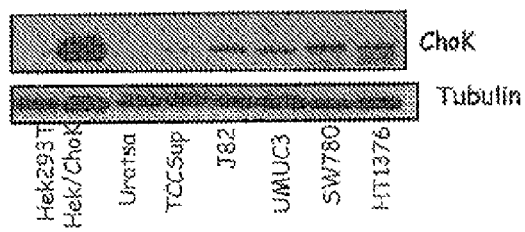
FIG. 19b: choline kinase alpha protein detected by immunoassay with a monoclonal antibody in normal immortalized bladder cells (UrotSa) and in cell lines derived from bladder cancer TCCsup, J82, UMVC3, SW789 and HT1376, as well as in a negative control (Hek293T cells) and in a positive control (Hek-ChoK cells, transfected with a plasmid expressing choline kinase alpha); the signal obtained for tubulin in the same samples is represented immediately under it.
Figure 19C:
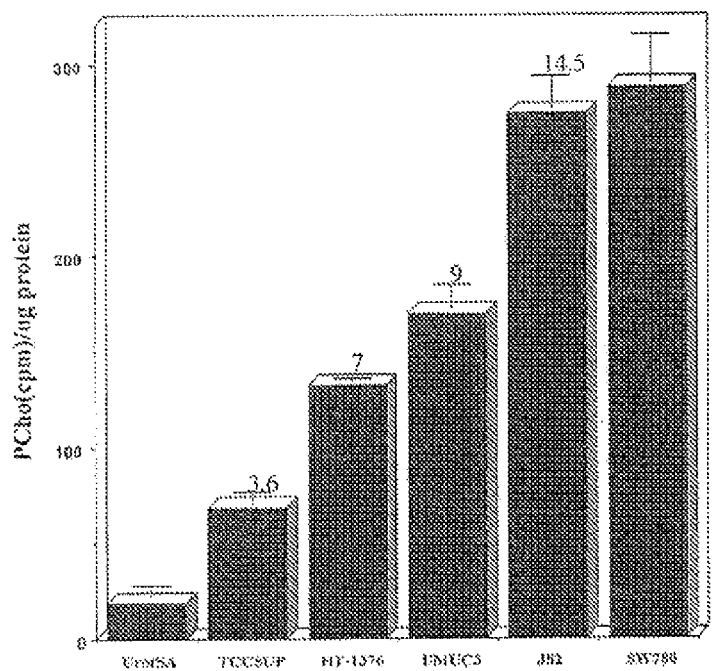
FIG. 19c: choline kinase activity represented by the radioactively marked PCho signal detected per microgram of protein after 30 minutes, generated from choline, marked in each of the cell lines indicated under the corresponding bars.

Analogous studies were also carried out in patients with bladder cancer. First, the mRNA levels corresponding to said enzyme in cell lines derived from patients with bladder cancer were detected, again by means of automated real-time quantitative PCR reactions with specific Taqman probes, similar to that described in Example 8 for the case of lung cancer. Lines HT1376, J82, SW780, TCCSup and UMVC3 were used, the data being represented in logarithmic scale in relation to normal immortalized bladder cells, UrotSa. The results are shown in FIG. 19a. The data was complemented with the detection data regarding the protein level in each of these cell lines by means of immunoassay with a monoclonal antibody (FIG. 19b) and the assessment of the detectable enzymatic activity therein (FIG. 19c). It can be observed that the different cell lines show increased ChoKα levels with respect to normal immortalized UrotSa cells, as well as that the increase of the expression of the protein in the cell lines derived from bladder cancer is also accompanied by a similar increase in the activity of the choline kinase enzyme.

Additionally, the antiproliferative effect of ChoK inhibition in these cell lines caused by the addition of MN58b was also checked, obtaining the results shown in the following Table, in which the numbers between parentheses indicate the induction factor with respect to the cell line with lover ChoK levels, TCCSup, as the data obtained for UrotSA were not considered to be sufficiently reliable for carrying out the comparison in relation thereto.

TABLE 3

Antiproliferative effect of Chok inhibition against
cell lines derived from human bladder cancer

| Cell line | TCCSup | HT1376 | UMUC3 | J82 | SW780 |
|---|---|---|---|---|---|
| IC50 ($\mu$M) (96 h) | 3.7 (1) | 2.49 (1.5) | 1.98 (1.86) | 1.08 (3.4) | 0.91 (4.1) |
| ChoK Expression | 2.5 (1) | 5 (2) | 5 (2) | 12.6 (5) | 12.6 (5) |
| ChoK Activity | 3.6 81) | 7 (1.9) | 9 (2.5) | 14.5 (4) | 15 (4.2) |

Figure 20A:
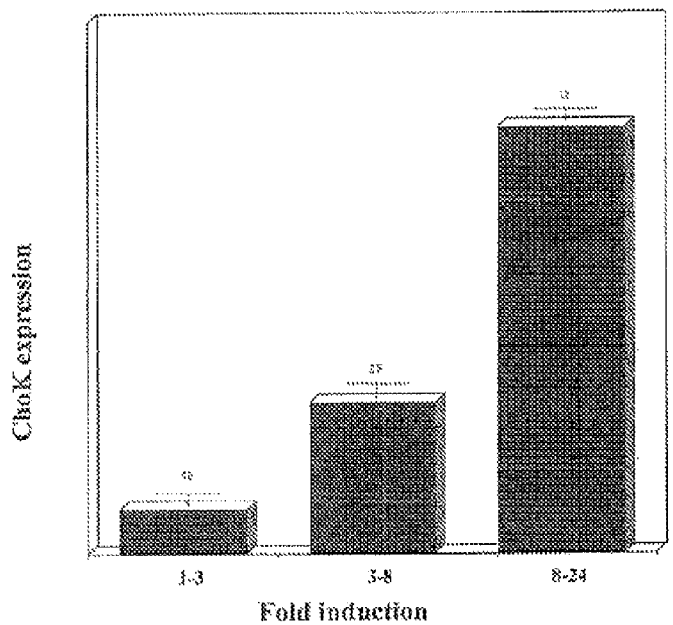
FIG. 20a: Mean expression values obtained from tumor tissues in 90 patients by means of microarray U133 Plus 2.0 of Affymetrix, obtained in the different groups classified according to the value of the induction factor: an induction of 1 to 3 times (first bar), an induction of 3 to 8 times or an induction of 8 to 24 times (third bar).

Furthermore, in order to establish parallelisms with the effects observed in vivo, ChoKα expression in tumor tissue in 90 patients with bladder cancer was analyzed using microarray technology, specifically the U133 Plus 2.0 chip of Affymetrix. The obtained results are shown in FIG. 20a. In said table it can be observed how a little over half, 49 patients, showed an expression induction factor of between 1 and 3 times; 25 patients showed an expression induction factor of between 3 and 8, whereas in 12 of them the expression induction factor was from 8 to 24 times.

Figure 20B:
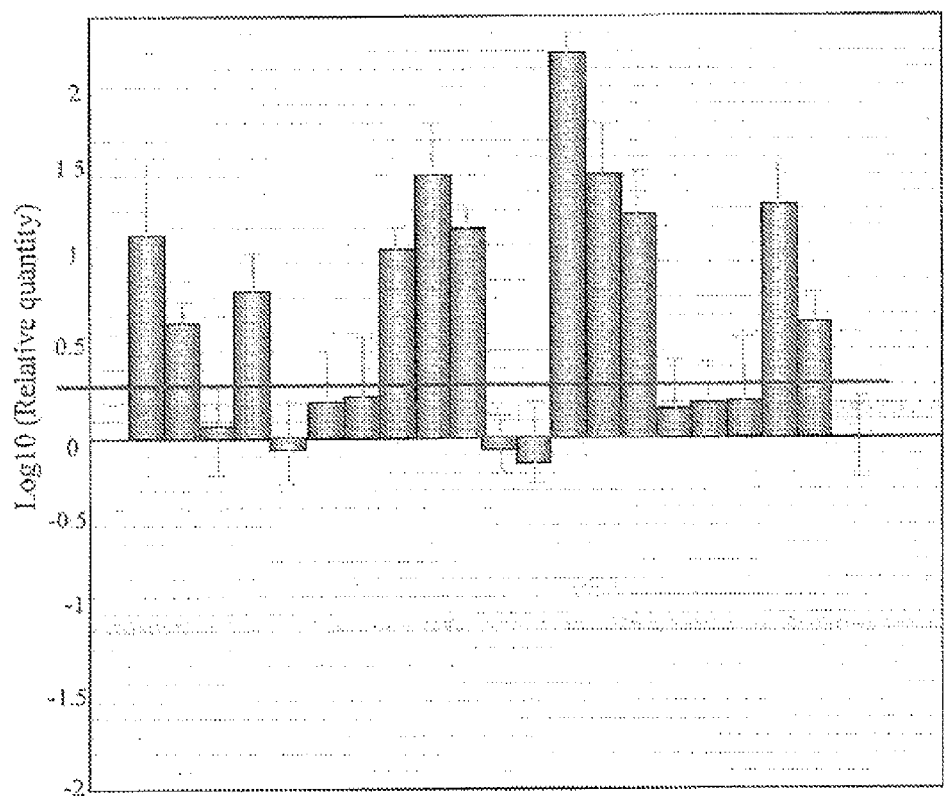
FIG. 20b: choline kinase alpha messenger RNA in 20 patients with bladder cancer, detected by real-time quantitative PCR, represented as base 10 logarithm of the ratio between the amount detected and the amount present in immortalized normal bladder UrotSa cells; the horizontal line represents the level from which there is an association with a worse prognostic evolution of the patient.

The data obtained with the microarray were validated by means of a real-time quantitative PCR assay (assay with Taqman probes), the results of which are shown in FIG. 20b. In said assay, commercial RNA from normal human bladder tissue was used as a reference, using GAPDH as endogenous control. In 18 of the 20 samples analyzed (10 of which corresponded to the 10 patients with lower ChoKα expression and the other 10 corresponded to the 10 patients with the highest expression), the ChoK expression results coincided with respect to the Affymetrix microarray and the analysis with Taqman probes. The incidence of ChoKα overexpression in tumors was 55%. The patients with overexpression were the most metastatic.

Figure 21A:
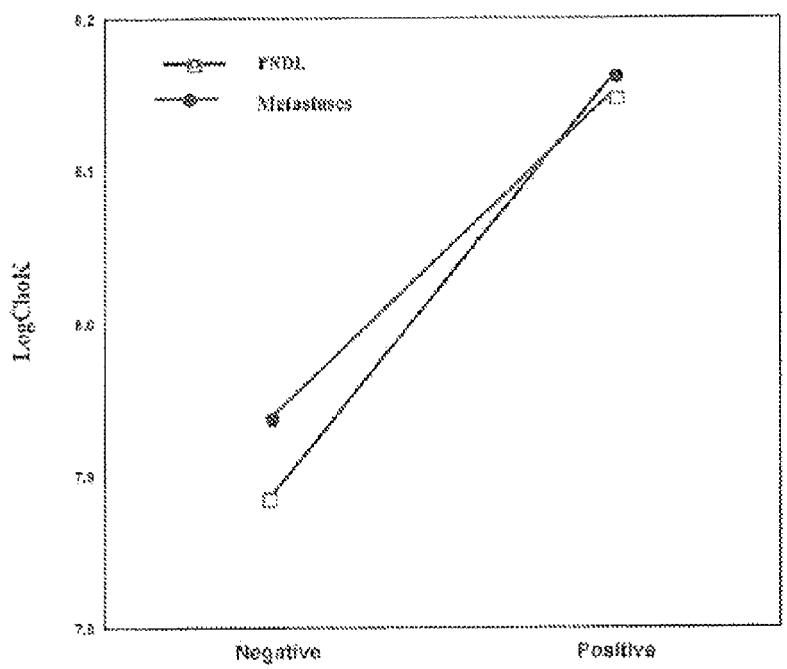
FIG. 21a: Mean choline kinase alpha expression levels in negative and positive patients with respect to the presence of lymphatic nodes (values marked with empty boxes, □) or metastasis (values marked with solid circles, ●); the straight lines join the mean values corresponding to positive or negative individuals with respect to the characteristic considered to aid in seeing the difference in level between the groups).
Figure 21B:
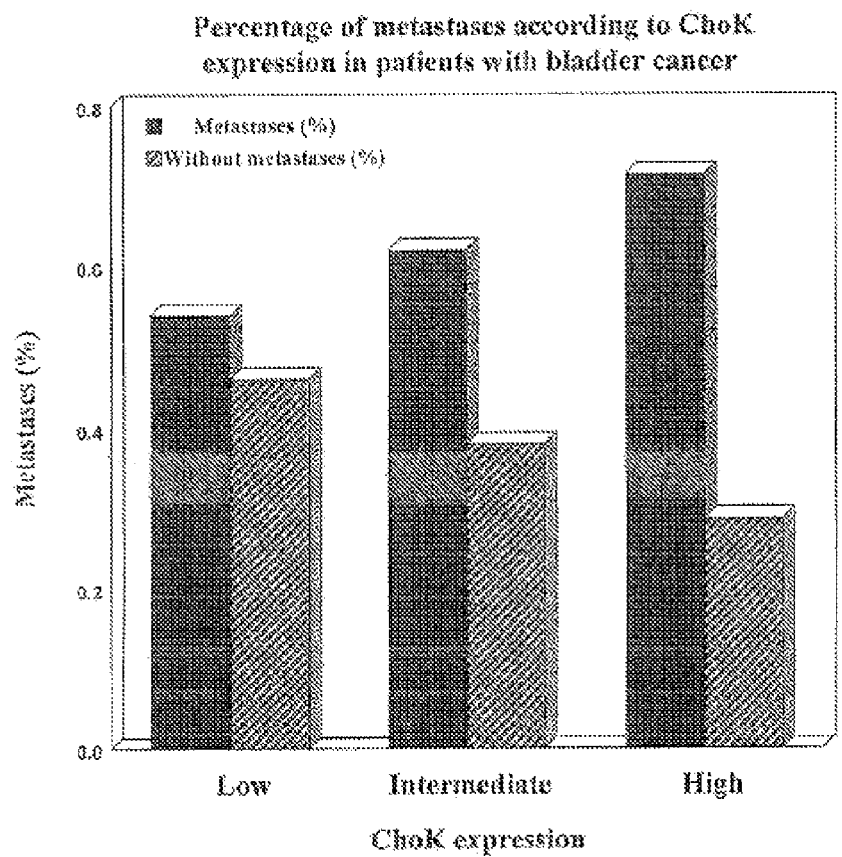
FIG. 21b: proportion of patients with metastases (bars with continuous dark color, ■) and without metastases (bars with slash marks, //) in groups of patients classified according to the choline kinase alpha expression level: low (pair of bars on the left), intermediate (pair of bars located in the middle of the graph) or high (pair of bars located on the right side of the graph).

The relationship between ChoKα overexpression and the progression of metastases was confirmed with the ChoKα expression data from all the patients obtained from the arrays, the results of which are shown in FIGS. 21a and 21b. FIG. 21a shows the variation in the mean ChoKα expression levels between the negative and positive patients with respect to the presence of lymph nodes (values joined by the line with blank squares at the ends) or the development of metastases (values joined by the line with solid circles at the ends). FIG. 21b, however, shows a graph representing the variation in the proportion of patients with metastases (bars with continuous dark color, ■) and without metastases (bars with slash marks, //) in the groups of patients with low ChoKα expression (low (pair of bars on the left), intermediate ChoKα expression (pair of bars located in the middle of the graph) or high ChoKα expression (pair of bars located on the right side of the graph), in which it can be seen how the percentage of patients with metastases (53%) in the low expression group is not much higher than that of patients without metastases (47%), whereas in the high ChoKα expression group, most of them, 72%, have metastasis and the remaining 28% do not. A relationship is observed between ChoKα expression and the development of metastases which does not reach the level of statistical significance.

To demonstrate the relevance of ChoKα overexpression in bladder cancer in vivo, an orthotopic bladder cancer model was also used which is physiologically very similar to what occurs when a tumor is generated in the bladder, using MBT-2 (mouse bladder tumor) cells. In these cells, which already have overexpressed ChoKα with respect to normal mouse cells, this protein is even more overexpressed for the purpose of evaluating if a greater ChoKα expression enhances the aggressiveness or invasiveness of these tumors. To that end, MBT-2 cells containing an empty vector, lacking sequences which allowed expressing the ChoKα gene (control group of mice, consisting of three mice), or MBT-2 cells overexpressing ChoKα by having been transfected with a vector with the sequence encoding for said enzyme (ChoKα group of mice, consisting of three mice), were directly inoculated in the bladder of the mice by means of a catheter. The generation of tumors was monitored in both groups by means of nuclear magnetic resonance with gadolinium contrast, as well as the evolution of the disease in the mice (physical condition, survival, histological study of the tumors, analysis of the possible invasion of the kidney and other organs . . . ). 19 days alter inoculating the cells, the ChoKα mice were in a poor condition, 2 of them with a very large tumor, whereas the mice that received the empty vector (control group) began to have a poor condition 50 days after inoculating the cells.

The results of Examples 7, 8 and 9 confirm that ChoKα is overexpressed with a high incidence in human breast, lung and bladder tumors. Its overexpression is associated with clinical parameters indicating greater malignancy: presence of lymphatic nodes, metastasis and low patient survival.

Example 10

Genetic Specificity

Inducible Interference Model

Given that the interference of ChoKα in tumor cells is lethal inducing cell death by apoptosis, as demonstrated in the assays described in Example 6, carried out in a transient assay, it is not possible to have a stable cell population expressing the interference construction in this type of study. A percentage of the variable cell population is affected in transient assays, the total population never being affected, which masks the results. It would be better to study the effect of the construction on a population that expressed it homogenously, so it would not be necessary to have a stable constitutional model. This makes it necessary to have an inducible interference model which allows obtaining a homogenously interfered population in ChoKα expression.

To obtain this, the interference sequence is expressed in a construction in which it is under a repressor which prevents its expression. The co-transfection of the inducible construction of interest together with a repressor which prevents its expression is carried out, and once a homogenous population is selected with this construction, the cells are treated with an inducer, which allows the expression of the interference of the construction and therefore the interference of the expression of the protein.

Figure 22:
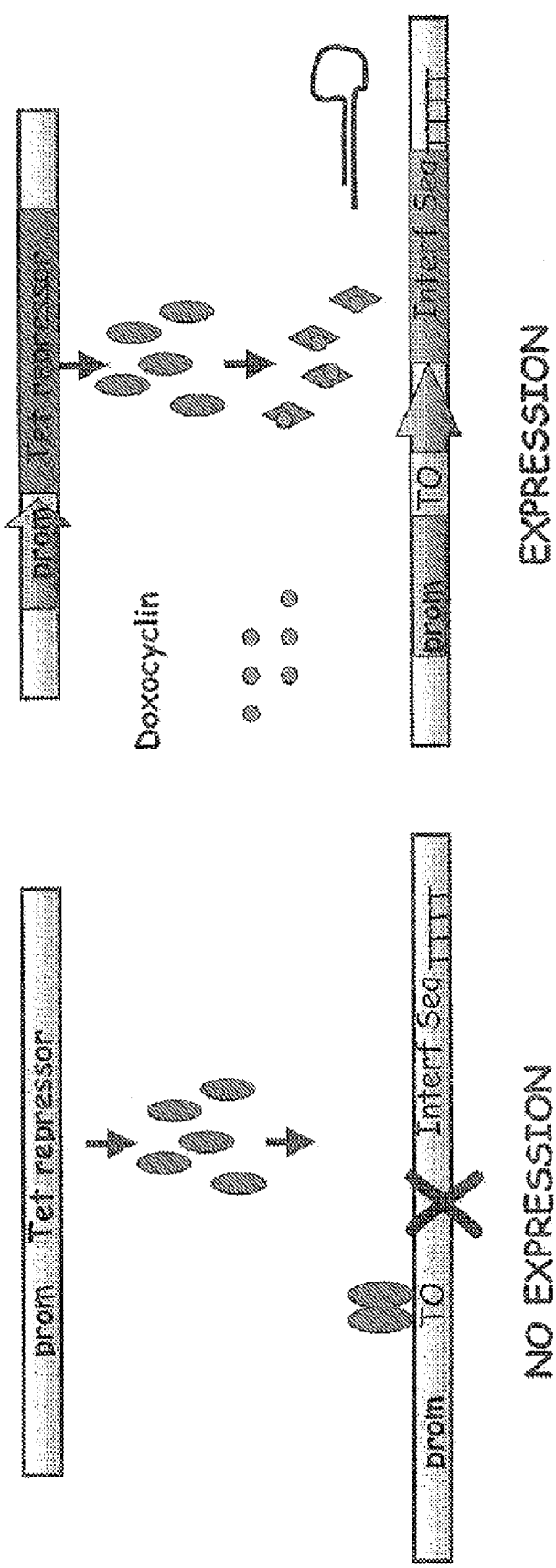
FIG. 22: Operating scheme of the construction based on which interference RNA can be synthesized. In the presence of repressor (left area, "No Expression", it binds to the construction and prevents RNA synthesis); in the presence of an inducer (doxocycline), it binds to the repressor, preventing its attachment to the interference construction and allowing synthesis of the interference RNA (right area, "Expression").

In the inducible model designed for this assay, the interference construction for ChoKα is expressed in the vector pSUPERIOR-pure (Oligoengine) and the repressor in the vector pcDNA6/TR (Invitrogen). The inducer used is doxocycline which, when binding to the repressor, prevents it from binding to the corresponding sequence, therefore the expression of the interference sequence is no longer prevented. A scheme of this system can be observed in FIG. 22.

Figure 23:
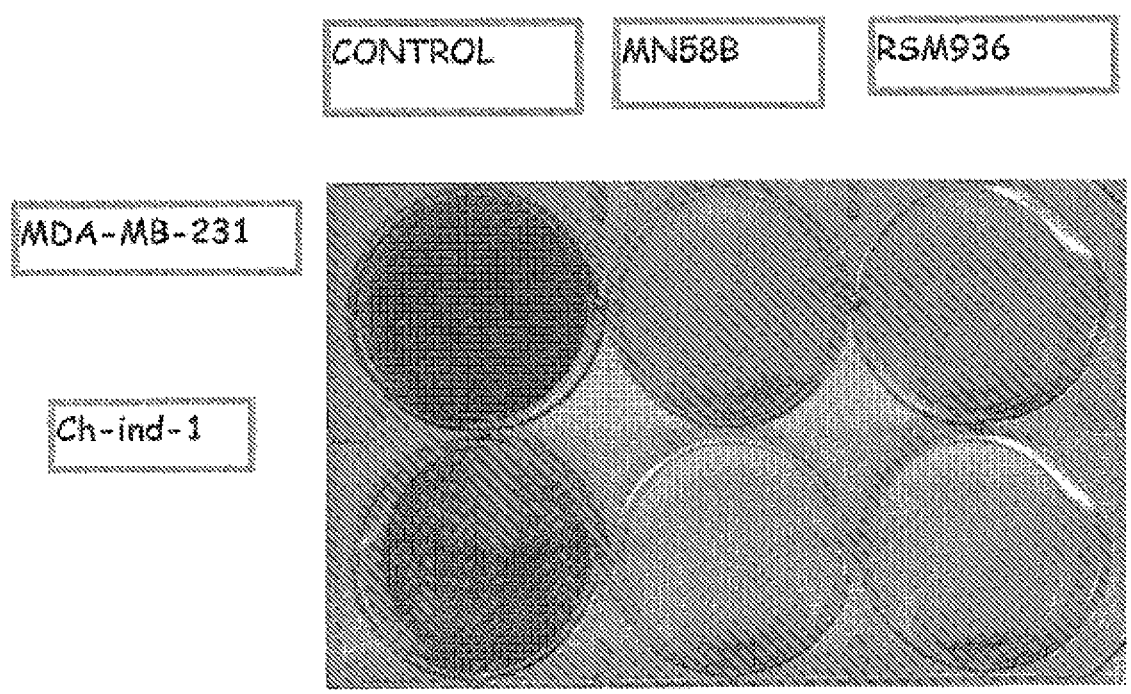
FIG. 23: Proliferation of MDA-MB-231 (upper row of plaques) and Ch-ind-1 (lower row of plaques) cells in growth permissive conditions ("Control" column) or in the presence of the chemical inhibitors of choline kinase MN58b (middle column) or RSM936 (right column).
Figure 24:
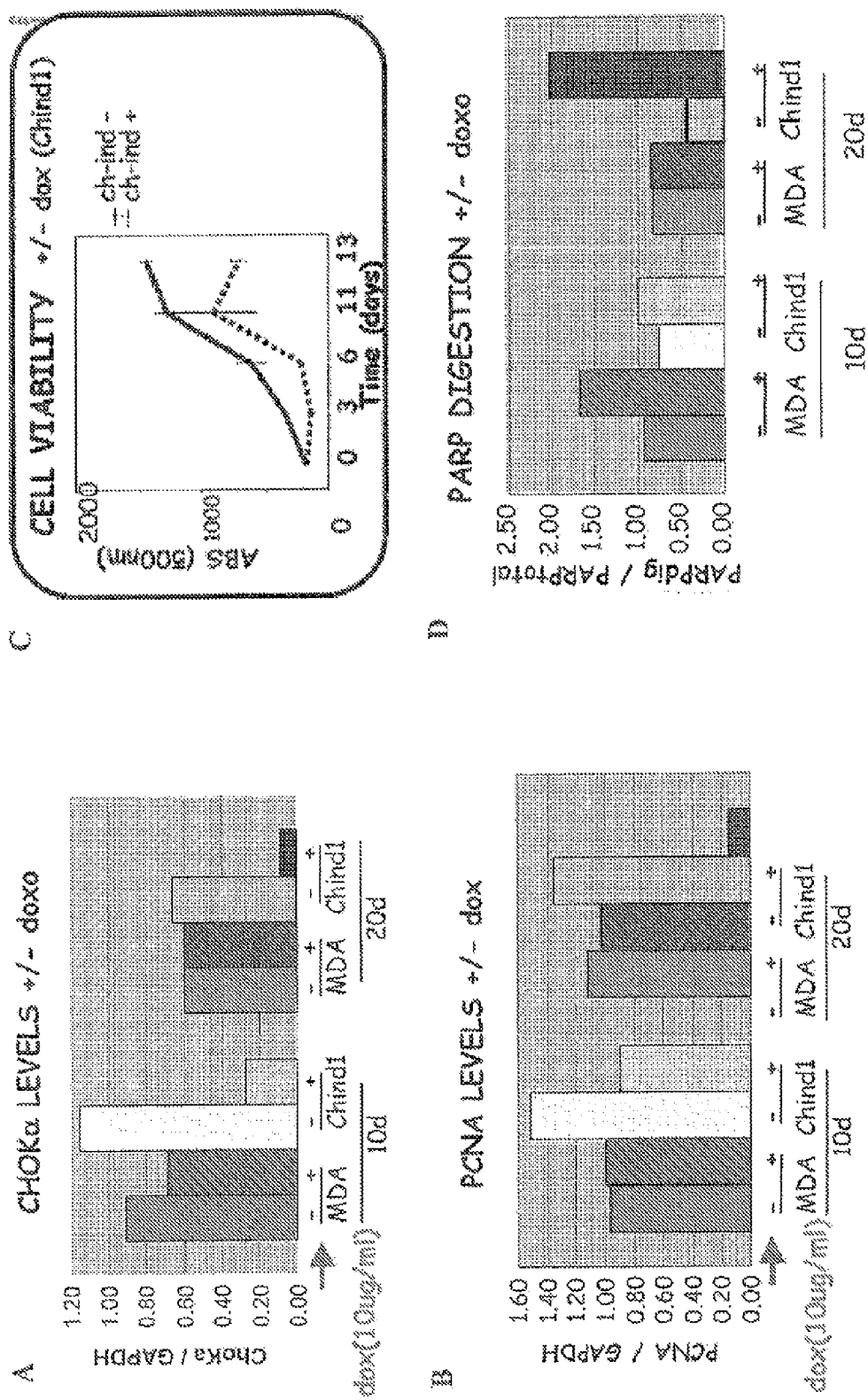
FIG. 24: Behavior or MDA-MB-231 (bars marked as "MDA") and Ch-ind-1 (bars marked as "Chind1") cells in the absence ("−") or presence "+" of 10 μg/ml of doxocycline, after 10 days ("10d") or 20 days ("20d"). A: Effect on the genetic inhibition of choline kinase alpha according to the ratio between the choline kinase alpha and GAPDH levels; B: Effect on cell proliferation, according to the ratio between the pCNA and GAPDH levels; C: Cell viability of the Ch-ind-1 cells in the absence (dotted line) or in the presence (continuous line) of an inducer, deduced from the absorbance values at 500 nm observed at different times; D: Effect on apoptosis induction, according to the ratio between the degraded PARP protein level with respect to the total PARP protein level (PARPdig/PARPtotal).

FIGS. 23 and 24 show the results obtained in Ch-ind-1 cells, a cell line derived from MDA-MB-231, capable of expressing the interference construction after treatment with the inducing agent doxocycline. FIG. 23 shows that this inducible line is still sensitive to the chemical inhibition of ChoKα in a manner similar to what occurs in MDA-MB-231 (the parent control line derived from breast adenocarcinoma from which Ch-ind-1 is generated), as the results obtained after treatment with the choline kinase inhibitors MN58b or RSM936 are analogous in both lines. FIG. 24, however, shows how the genetic inhibition of ChoKα occurs only in Ch-ind-1 when treating both cell lines with 10 μg/ml of doxocycline, as the induction of the interference model with doxocycline can only occur in line Ch-ind-1, because it is the one having a construction from which the synthesis of interference RNA can occur when the binding of the repressor is prevented. The genetic inhibition of ChoKα is correlated with a reduction of cell proliferation (determined by pCNA) and an increase of cell death due to apoptosis (determined by PAR-Pdig, degraded PARP protein, which is an indicator of apoptosis). The effect begins to be seen after 10 days, although it is still very initial, and is much more pronounced 20 days after the beginning of the experiment (in which the population has very little ChoKα expression).

The results obtained with the inducible model corroborate the data previously obtained in transient, showing that the observed effects are due to the specific inhibition on ChoKα.

Example 11

Evaluation of the Possible Effect of Chokβ Overexpression in Carcinogenesis

Several assays were carried out to evaluate the possible effect that choline kinase beta (ChoKβ) overexpression may have in carcinogenesis and to confirm if the increase of choline kinase activity observed in different cancerous tissues and cell lines derived from cancerous tissues could be attributed exclusively to choline kinase alpha or if choline kinase beta also participated.

Figure 25:
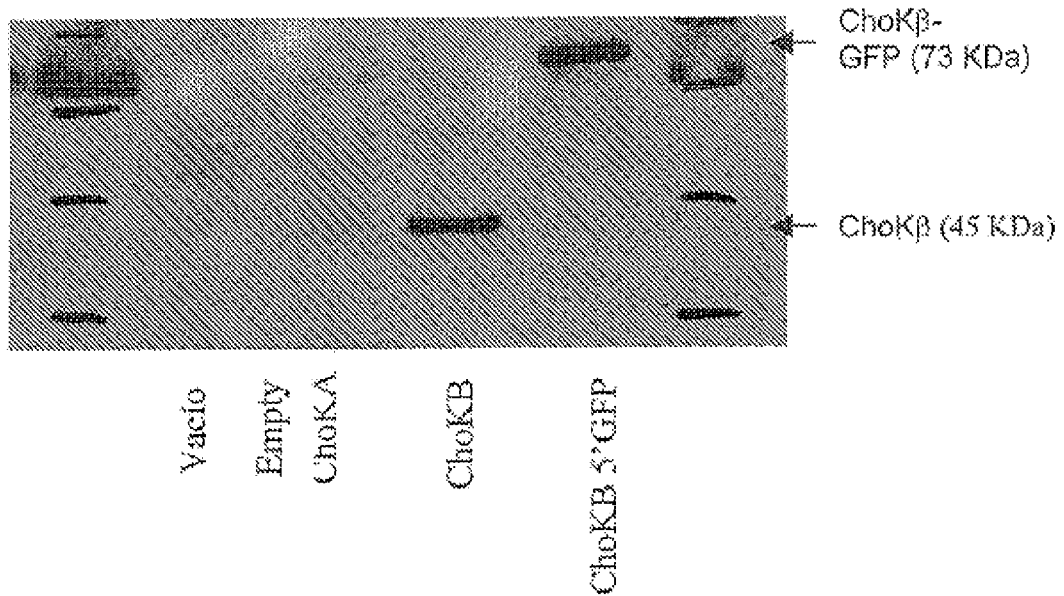
FIG. 25: Specificity of the polyclonal antibody against choline kinase beta. A: Immunoassay in which an anti-choline kinase beta polyclonal antiserum interacts with samples of cells transfected with an empty vector (lane called "empty"), a choline kinase alpha expression vector (lane called "ChoKA"), a choline kinase beta expression vector (lane called "ChoKB") and a chimeric protein, choline kinase beta-green fluorescent protein, expression vector (lane called "ChoKB5'GFP"). The arrows indicate the banding height of choline kinase beta and of the chimeric protein. B: Immunoassay in which an anti-choline kinase alpha polyclonal antibody interacts with samples of cells transfected with an empty vector (lane called "empty"), a choline kinase alpha expression vector (lane called "ChoKA"), a choline kinase beta expression vector (lane called "ChoKB") and a chimeric protein, choline kinase beta-fluorescent green protein, expression vector (lane called "ChoKB5'GFP"). The arrows indicate the banding height of choline kinase alpha.
Figure 25:
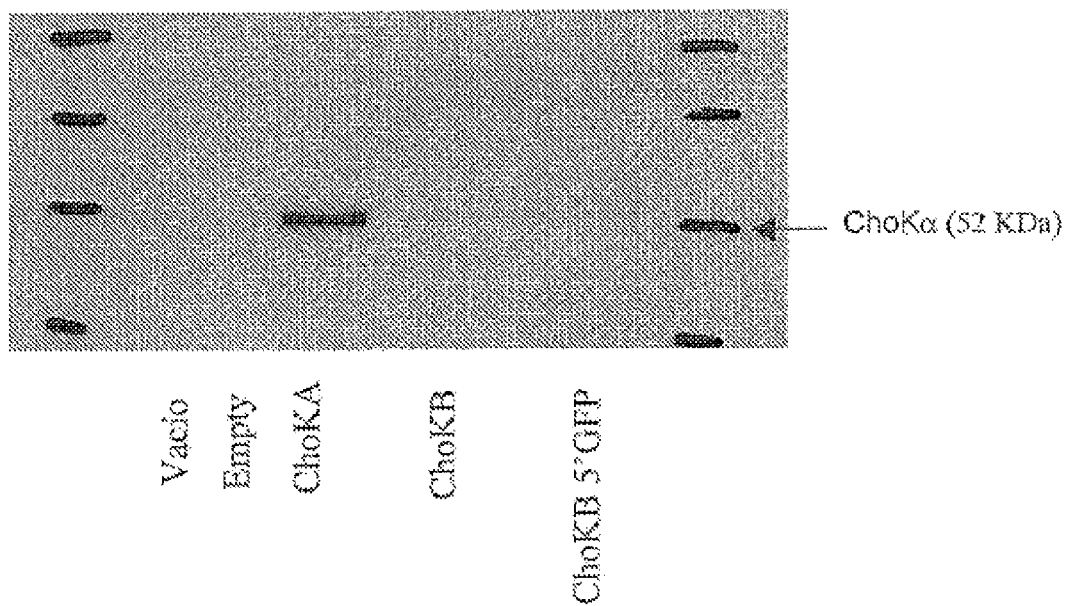

First a polyclonal anti-ChoKβ1 antibody was generated. The specificity thereof was checked in three groups of transfected Hek293T cells, one of which was transfected with a construction from which ChoKα expression was produced, a second one transfected with a construction that allowed the expression therein of ChoKβ, and the third one with a construction in which a chimeric protein ChoKα-GFP was expressed, as well as in a group of control cells transfected with an empty vector. As can be seen in part A of FIG. 25, the immunodetection assays showed the specificity of said antibody, which gave way to a signal both in the cells that expressed ChoKβ and in the cells that expressed the chimeric protein ChoKβ-GFP, without a signal occurring in the lane corresponding to the cells transfected with the construction for ChoKα expression; in these latter cells, however, a monoclonal antibody directed against ChoKα give rise to a signal in a band which occurred at the height corresponding to ChoKα.

Figure 26:
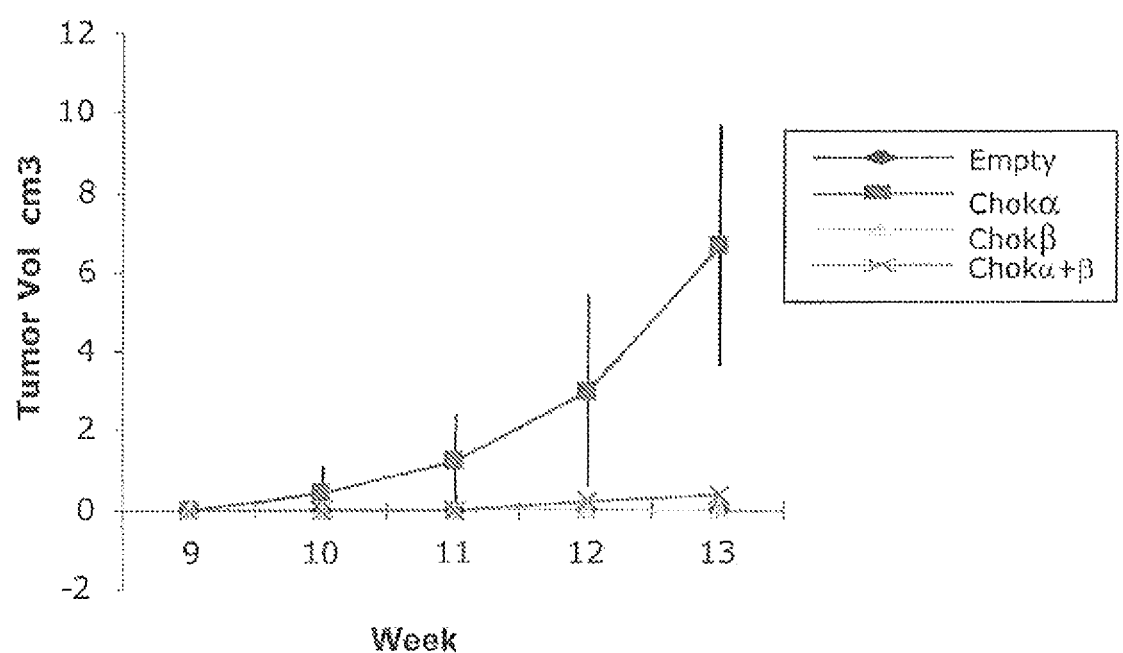
FIG. 26: Comparison of the tumorigenic capacity of choline kinases alpha and beta. Evolution of the tumor volume, measured in square centimeters; according to the weeks indicated on the x-axis, elapsing from the injection in mice of cells transfected with: an empty vector (data indicated with diamonds "♦"), a choline kinase alpha expression vector (data indicated with squares, "■"), a choline kinase beta expression vector (data indicated with triangles, " ") and a choline kinase alpha expression vector+a choline kinase beta expression vector (data indicated with an x, "X").

In order to check the possible effect of ChoKβ on carcinogenesis, it possible transforming activity was assayed in vivo. To that end, athymic mice (Nu/Nu) were used again that were injected with a million transfected human HEK293T cells, either with an empty vector as a control, with a choline kinase alpha expression vector, or with a choline kinase beta expression vector and, in a last group, the co-transfection of the vectors which expressed each of the choline kinase alpha and beta isoenzymes was produced. The tumor growth was monitored at least twice a week for 13 weeks after the injection. As can be observed in FIG. 26, a clear induction of tumors was observed in the animals that had received the cells transfected with the ChoKα expression vector, no induction of tumors being observed in the mice that received the cells transfected with the ChoKβ expression vector. It is striking to observe that in the mice that received cells transfected with both vectors, the ChoKα and ChoKβ expression vectors, a slight induction of tumors was observed with a magnitude that was much less than that observed with ChoKα expression alone and observed more than 11 weeks after the injection of the transfected cells, which may indicated that ChoKβ may be directly or indirectly regulating ChoKα such that it inhibits its oncogenic activity.

Figure 27:
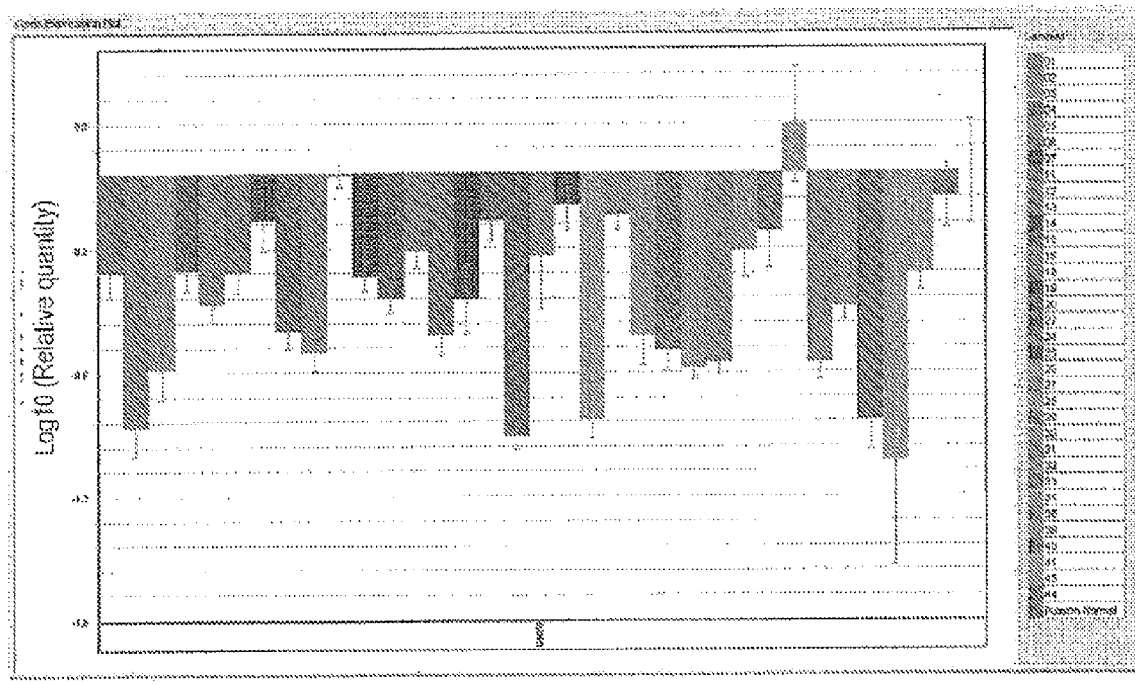
FIG. 27: Choline kinase beta messenger RNA in tissue of patients with lung cancer, detected by real-time quantitative PCR, represented as base 10 logarithm of the ratio between the amount detected and the amount present in normal tissue.

This data was complemented by seeing if there was overexpression of the choline kinase beta enzyme in tissues extracted from patients with cancer. FIG. 27 shows the data obtained in lung samples from patients operated on after isolating messenger RNA therefrom and carrying out automated real-time quantitative PCR reactions with specific Taqman probes, representing the obtained data in a base 10 logarithmic scale with respect to a normal tissue control sample. In said figure it can be observed how ChoKβ expression decreases with respect to that obtained in normal tissue in most of the analyzed samples, unlike what occurs with ChoKα.

This data does not suggest that there was a correlation between choline kinase beta overexpression and the generation and development of tumors.

All the results indicated in the examples specifically support choline kinase alpha as a new therapeutic target in the treatment of neoplastic diseases.

The invention claimed is:
1. An in vitro method for determining the survival time of a patient with cancer comprising:
   a) measuring a level of choline kinase alpha activity in a cancerous tissue sample extracted from the patient by determination of at least one parameter in said sample related to the choline kinase alpha activity selected from the group consisting of a level of choline kinase alpha messenger RNA using an amplification based assay and a concentration of choline kinase alpha protein using an immunoassay;
   b) measuring a level of choline kinase alpha activity in one or more normal non-cancerous tissue samples by determination of at least one parameter in said sample related to the choline kinase alpha activity selected from the group consisting of a level of choline kinase alpha messenger RNA using an amplification based assay and a concentration of choline kinase alpha protein using an immunoassay;
   c) comparing the levels measured in a) and b); and
   d) determining a decreased survival time when the level measured in a) is higher than the level measured in b) or an increased survival time when the level measured in a) is the same or lower than the level measured in b).
2. The method of claim further comprising:
   a) determining the level of choline kinase alpha messenger RNA by amplifying the mRNA present in a total RNA extract from the cancerous tissue sample to produce an amplification product; and
   b) quantifying the amplification product of the mRNA.
3. The method of claim 2, wherein the level of mRNA is measured by real time quantitative PCR.
4. The method of claim 1, wherein the cancer is lung cancer.
5. The method of claim 1, wherein the cancer is breast cancer.
6. The method of claim 1, wherein the cancer is bladder cancer.

* * * * *